US008271294B2

(12) United States Patent
Eisenberger et al.

(10) Patent No.: US 8,271,294 B2
(45) Date of Patent: Sep. 18, 2012

(54) PUBLISHER GATEWAY SYSTEMS FOR COLLABORATIVE DATA EXCHANGE, COLLECTION, MONITORING AND/OR ALERTING

(75) Inventors: George Eisenberger, White Plains, NY (US); Edgar H. McCulloch, III, Arlington, VA (US); Thomas L. Richards, II, Chicago, IL (US)

(73) Assignee: International Businesss Machines Corporation, Armonk, NY (US)

( * ) Notice: Subject to any disclaimer, the term of this patent is extended or adjusted under 35 U.S.C. 154(b) by 24 days.

(21) Appl. No.: 12/147,276

(22) Filed: Jun. 26, 2008

(65) Prior Publication Data
US 2008/0288294 A1 Nov. 20, 2008

Related U.S. Application Data

(63) Continuation of application No. 11/032,664, filed on Jan. 10, 2005, now abandoned.

(51) Int. Cl.
*G06Q 50/00* (2012.01)
(52) U.S. Cl. ........... 705/2; 705/3; 705/7.11; 600/300
(58) Field of Classification Search ............... 705/2, 3; 600/300
See application file for complete search history.

(56) References Cited

U.S. PATENT DOCUMENTS

| | | | | |
|---|---|---|---|---|
| 5,557,514 A * | 9/1996 | Seare et al. | ............ | 705/2 |
| 5,560,005 A | 9/1996 | Hoover et al. | | |
| 5,891,049 A * | 4/1999 | Cyrus et al. | ............ | 600/523 |
| 5,924,074 A * | 7/1999 | Evans | ............ | 705/3 |
| 6,018,713 A * | 1/2000 | Coli et al. | ............ | 705/2 |
| 6,108,635 A * | 8/2000 | Herren et al. | ............ | 705/2 |
| 6,640,211 B1 * | 10/2003 | Holden | ............ | 705/64 |
| 6,789,091 B2 * | 9/2004 | Gogolak | ............ | 1/1 |
| 6,915,265 B1 | 7/2005 | Johnson | | |
| 7,299,192 B2 * | 11/2007 | Luttrell | ............ | 705/3 |
| 2002/0091548 A1 * | 7/2002 | Auer et al. | ............ | 705/3 |
| 2002/0095399 A1 | 7/2002 | Devine | | |
| 2002/0128871 A1 | 9/2002 | Adamson et al. | | |
| 2003/0135394 A1 | 7/2003 | Padron et al. | | |
| 2004/0078236 A1 * | 4/2004 | Stoodley et al. | ............ | 705/2 |
| 2005/0071194 A1 * | 3/2005 | Bormann et al. | ............ | 705/2 |
| 2005/0119914 A1 * | 6/2005 | Batch | ............ | 705/2 |
| 2008/0255885 A1 | 10/2008 | Eisenberger et al. | | |
| 2008/0256248 A1 | 10/2008 | Eisenberger | | |
| 2008/0288466 A1 | 11/2008 | Eisenberger | | |

OTHER PUBLICATIONS

International Search Report, dated Aug. 18, 2006 for related PCT application No. PCT/EP2006/050025.
Rule 132 Declaration of George Eisenberger of Pre-Patent Filing Activity, 3 sheets, executed Dec. 5, 2005.
Nardone, B., The healthcare Collaborative Network, Its worth can be calculated in lives saved, Healthcare Informatics Online, The McGraw-Hili Companies, 4 sheets, Jan. 2004.

(Continued)

*Primary Examiner* — David Rines
(74) *Attorney, Agent, or Firm* — Steven L. Nichols; Van Cott, Bagley, Cornwall & McCarthy P.C.

(57) ABSTRACT

A Publisher source of healthcare data is configured to communicate with an Internet-based data sharing system, the Publisher comprising a Publisher Gateway configured to electronically receive patient data from a plurality of data input sources, automatically correlate data from the plurality of input sources associated with respective patients into respective electronic patient data records having electronically searchable data fields, and electronically store the patient data records in a Publisher database.

21 Claims, 28 Drawing Sheets

OTHER PUBLICATIONS

Brewin, B., New Health Data Net May Help in Fight Against SARS, Computerworld, 2 sheets, Apr. 28, 2003.
Brewin, B., Health collaborative backs standards-based records, launches new pilot network, Computerworld, 2 sheets, Jun. 5, 2003.
Aul T, A., New Healthcare data sharing project uses IBM technology, Reuters-Health, 2 sheets, Jun. 5, 2003.
Sarkar, D., Health group pushes info sharing, Federal Computer Week, 2 sheets, Jun. 5, 2003.
Connor, D., Healthcare network aims to improve patient care, NetworkWorldFusion, 1 sheet, Jun. 5, 2003.
Healthcare Collaborative Launched to Demonstrate Technical Feasibility and Value of Standards-Based Electronic Model of Data Interchange, Business Wire, 3 sheets, Jun. 5, 2003.
Healthcare Collaborative Network Components, displayed on board in vendor area of event held in Jun. 2003 at the Washington Press Club, 3 sheets, Jun. 2003.
Brown, et al., Quick Take, Healthcare ITs Next Big Market, Cerner Buys Vital Works, Moving from Hospital to Physician to Community, 4 sheets, Nov. 30, 2004.
Non-Final Office Action dated Jun. 10, 2009 for U.S. Appl. No. 11/032,405.
Non-Final Office Action dated Apr. 3, 2009 for U.S. Appl. No. 11/032,590.
Supplemental Rule 132 Declaration of George Eisenberger of Pre-Patent Filing Activity, 1 sheet, executed Dec. 5, 2005.
Rule 132 Declaration of George Eisenberger of Pre-Patent Filing Activity, 2 sheets, executed May 17, 2005.
Non-Final Office Action dated Mar. 18, 2010 for U.S. Appl. No. 11/032,391.
Final Office Action dated May 14, 2010 for U.S. Appl. No. 12/147,257.
Non-Final Office Action dated Oct. 9, 2009 for U.S. Appl. No. 12/147,257.

* cited by examiner

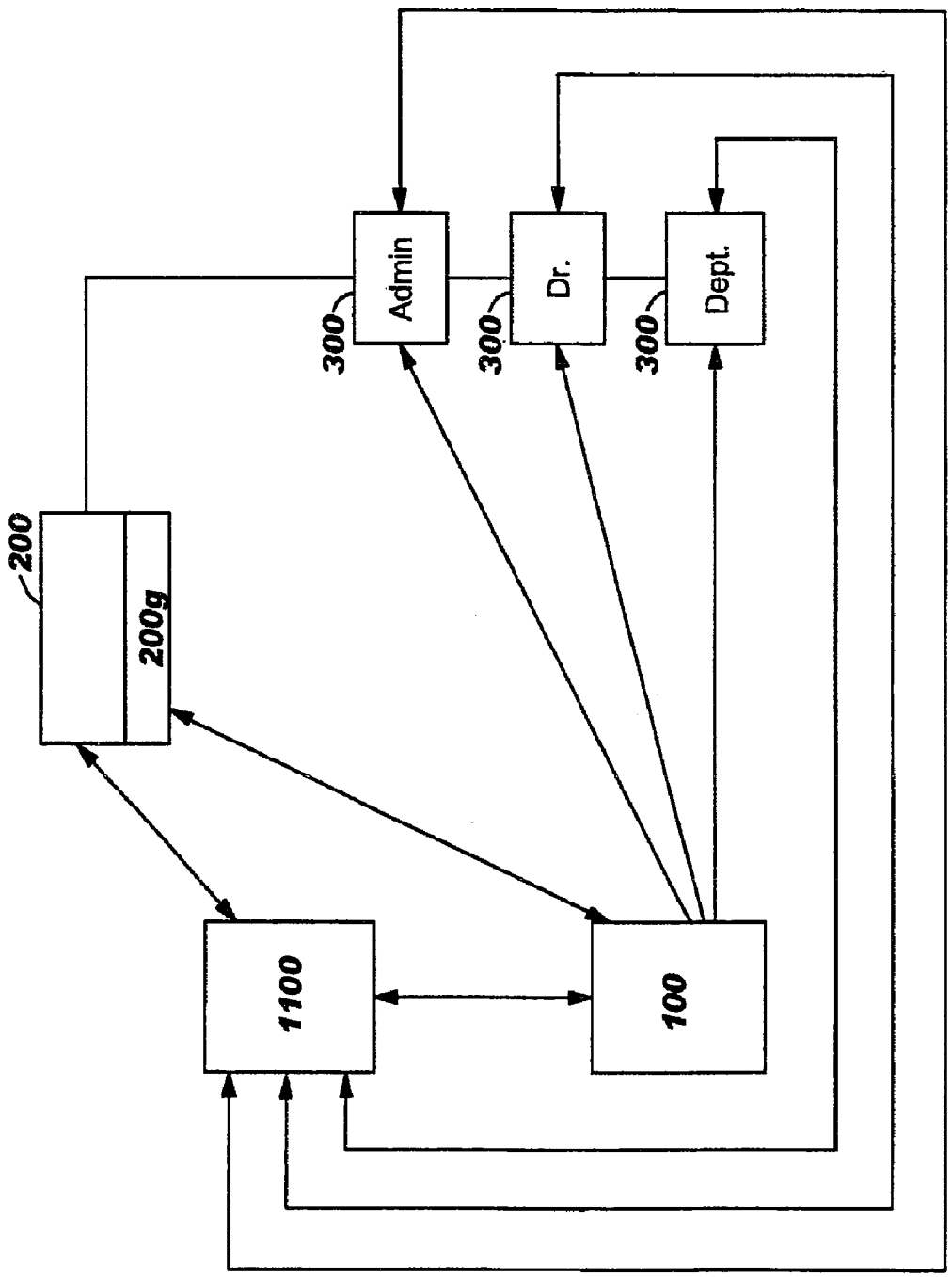

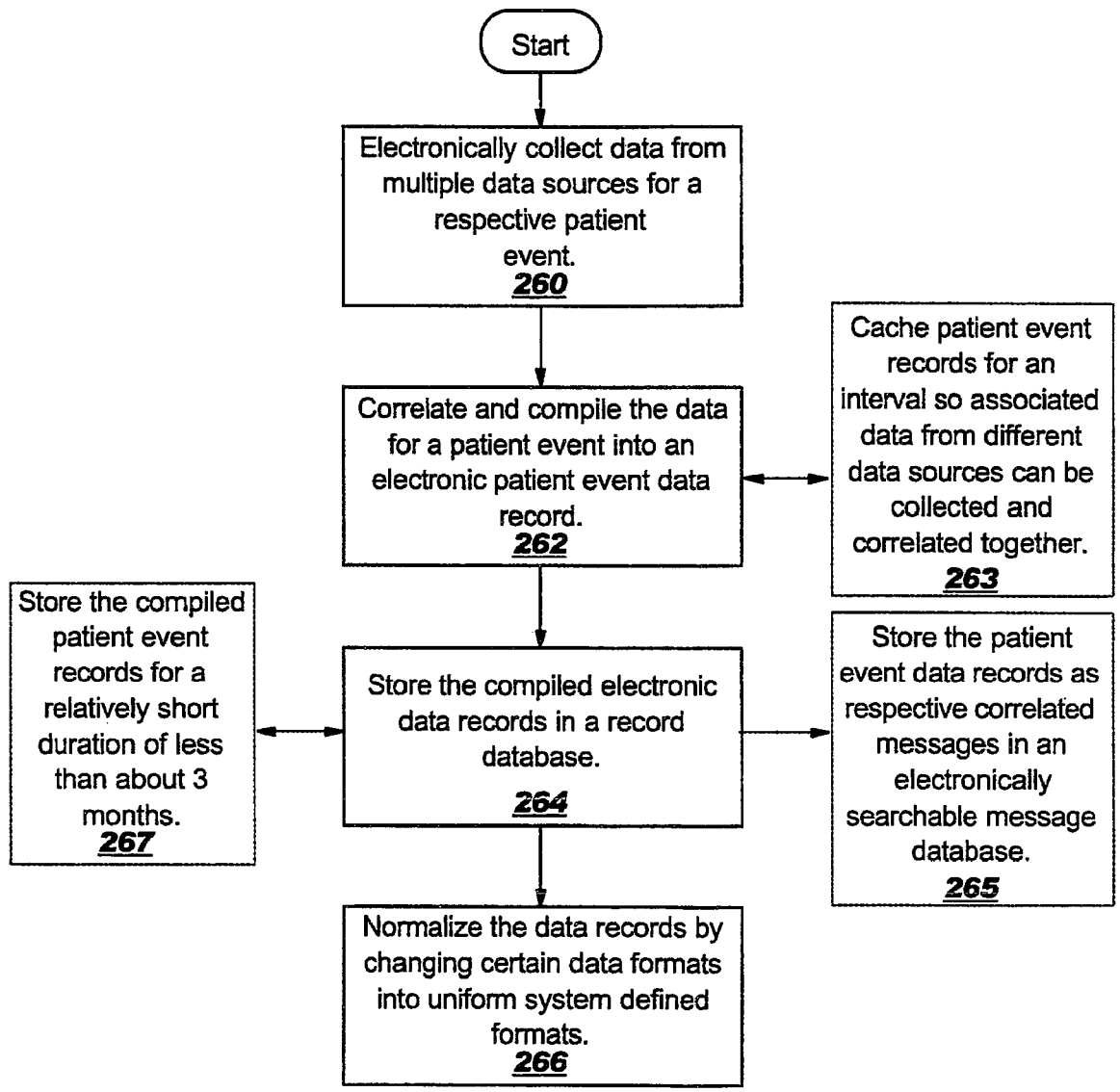

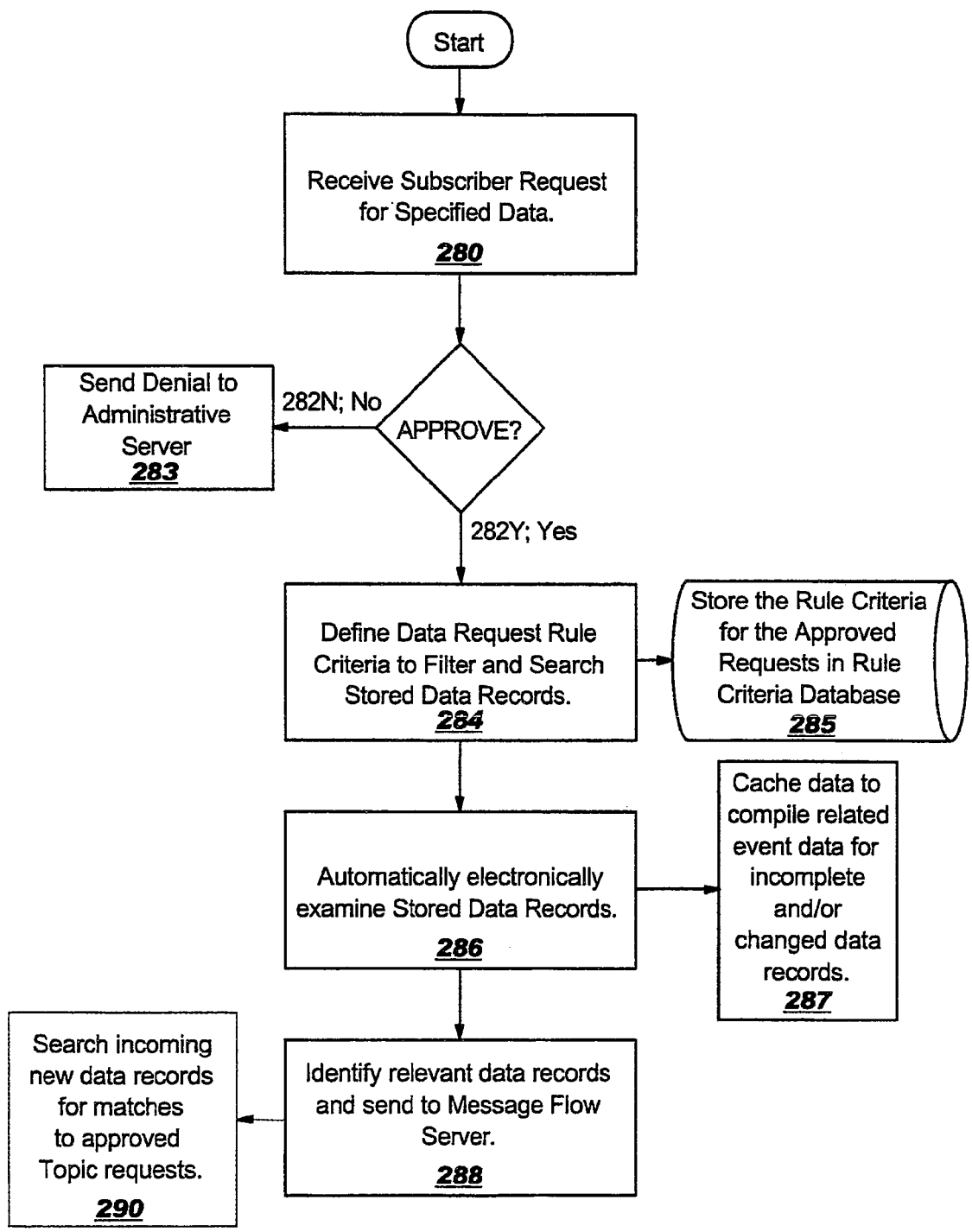

Sample Data Flow Summary - Aggregate Messages by Date

FIG. 13

Sample HCN Message includes Labs, Pharmacy, and Diagnosis Records for Patient

Message submitted successfully for publication:
Submission time: YYYY-DY-MO 12:25:09 09.921
Publisher ID: 'Provider 1'
Publish Topic: 'Stroke Diagnosis'
Rule Name: 'Stroke Diagnosis'
Patient ID: '123153'
Message Timestamp: 'YYYY-DY-MOT12:26:17-07-00'

'MSH|^~\&|<XXX>||<XXX>||20030719084337||RDE^O11|||<XXX>|2.4|
PID|||123153^^^&Provider 1|<XXX>|<XXX>||<XXX>|F|||||<XXX>|<XXX>|
PV1|||<XXX>|||<XXX>|<XXX>|<XXX>|||||HNA|||<XXX>|<XXX>|||||<XXX>|
ORC|NW|100|1849155||SC||^QD&0900^INDEF^20030719090000^R^0||20030719083900^R^0||20030719083900||<XXX>|<XXX>|<XXX>|<XXX>|
RXE||00004291600^PANTOPRAZOLE EC TAB 40 MG^L|40||^MG|TABLET EC|||1|EA|
RXR|^ORAL|.

'MSH|^~\&|<XXX>||<XXX>||20030719084337||ORU^R01|<XXX>|<XXX>|2.4|
PID|||123153^^^&Provider 1|<XXX>|||<XXX>||F||||||<XXX>|
OBR|||T44676BCBLUD037F^|600-7^LOINC^BLOOD
CULTURE||20030715160000|||||<XXX>|<XXX>|<XXX>|||||<XXX>|P||^^^^R|<XXX>|
OBX|1|TX36484^BLUD^MED|0|SPECIMEN DESCRIPTION: BLOOD|||||F|
OBX|2|TX|60187^NGB4^MED|0|CULTURE: NO GROWTH OF BACTERIA OR FUNGI AFTER 4 DAYS|||||F|

'MSH|^~\&|HIHLS21-215259|EAGLE 2000||20030731200333||ADT^A08|20030727024001798320|P|2.3|||NE|NE|
EVN|A08|<XXX>||<XXX>|<XXX>|
PID|<XXX>|||123153^^^&Provider 1||<XXX>|||<XXX>|F|<XXX>|||<XXX>|<XXX>|<XXX>|<XXX>|<XXX>|<XXX>|
DG1|<XXX>||9|430^SUBARACHNOID HEMORRHAGE^19|<XXX>|<XXX>|A|<XXX>|<XXX>|||||<XXX>|
DG1|<XXX>||9|430^SUBARACHNOID HEMORRHAGE^19|<XXX>|<XXX>|<XXX>|P|
DG1|<XXX>||9|401.9^HYPERTENSION NOS^19|<XXX>|<XXX>|S|
DG1|<XXX>||9|307.9^SPECIAL SYMPTON NEC/NOS^19|<XXX>|<XXX>|2.3|||<XXX>|<XXX>|
'. 'MSH|^~\&|<XXX>||<XXX>||||20030723190145||ADT^A03|<XXX>|<XXX>|2.3|||<XXX>|F|<XXX>|||<XXX>|<XXX>|<XXX>|<XXX>|<XXX>|
EVN|A03|<XXX>||<XXX>|<XXX>|
PID|<XXX>|||123153^^^&Provider 1||<XXX>|||<XXX>|F|<XXX>|||<XXX>|<XXX>|<XXX>|<XXX>|<XXX>|<XXX>|

FIG. 14

Sample view of notifications on the HCN Portal

Healthcare Collaboration Network
File Edit View Favorites Tools Help

◀ Back ▶ ⊗ ☐ ⌂ Search Address [_____] Go  Links  Google  Hotmail  PDC-W3 hcn
Healthcare Collaboration Network                                        • home    • help
Welcome:  Publisher  Role: | Publisher ▼ | Change Role                  • contact us • log out
                                                                        • legal               IBM
| Publications | Publication Requests | Authorization Requests | Health Topics | HCN Notifications | Participants |

NHCN Notifications
Click on a subject title to view the Notification Details.

| Date | Time | Type | From | Subject |
|------|------|------|------|---------|
| 03/26/YY | 12:00 | Email | Administrator | System Unavailable |
| 03/25/YY | 13:25 | Information | Administrator | Publication added to topic Anthrax |
| 03/25/YY | 15:44 | Information | "A" General Hospital | New Health Topic Diabetes has been added |
| 03/24/YY | 10:27 | Email | "A" General Hospital | New Health Topic Diabetes has been added |
| 03/23/YY | 11:11 | System | "A" General Hospital | New Health Topic Diabetes has been added |
| 03/23/YY | 16:03 | System | "A" General Hospital | New Health Topic Diabetes has been added |

→ more NHCN notifications

Publications                                                    Create Publication
Display Publications:
● All publications
○ Containing the word: [_____] Display
                                                    → more publications

Publication Requests
The following table lists subscriber requests for publications

| Topic Name | Requesting Organization |
|------------|-------------------------|
| Accutane with no pregnancy test | FDA |
| ADR for Accutane | FDA |
| ADR for Accutane | Centers for Medicare and Medicaid |

→ more publication requests

Authorization Requests
The following table lists subscriber requests for publications

| Topic Name | Requesting Organization |
|------------|-------------------------|
| Accutane with no pregnancy test | FDA |
| ADR for Accutane | FDA |
| ADR for Accutane | Centers for Medicare and Medicaid |

→ more authorization requests

Health Topics
Display Topics:
● All topics
○ Containing the word: [_____] Display
                                                    → more health topics

Participants
Display Participants:
● All participants
○ Beginning with letters: [_____] Display
                                                    → more participants

| home | contact us | legal | help | log out |                        Internet

FIG. 15

Sample view of reporting activity summary on the HCN Portal hcn
Healthcare Collaboration Network

Welcome: name Publisher    Role: Publisher ▶ Change Role

Publications | Publication Requests | Authorization Requests | Health Topics | HCN Notifications | Participants Health Topics
Display Publications:
● All publications
○ Containing the word: [    ] [Display]

| Topic Name | Topic Description |
|---|---|
| Accutane with no pregnancy test | Prescription of Isotretinoin for female with no pregnancy test administered. |
| ADR for Accutane | Prescription of Isotretinoin for a pregnant female. |
| ADR for Arava | A patient prescribed leflunomide (Arava) has elevated levels of AST and bil ... |
| ADR for Arava(2) | A patient prescribed leflunomide (Arava) has elevated levels of AST and bil ... |
| ADR for Clozapine | Agranulocitosis (as measured by neutrophil count) in connection with pres ... |
| ADR for Felbatol | A patient prescribed felbamate (Felbatol) has decreased red blood cell coun ... |
| ADR for Felbatol(2) | A patient prescribed felbamate (Felbatol) has decreased red blood cell coun ... |
| ADR for Felbatol(3) | A patient prescribed felbamate (Felbatol) has decreased red blood cell coun ... |
| ADR for Thalidomide | Prescription of thalidomide (Thalomid) for a pregnant female |
| AMI with ACE Inhibitor | A patient with a diagnosis of Acute Myocardial Infarction received an ACE In ... |

◀ PREV  Page 1 of 49  NEXT ▶
page [    ] [Go]

FIG. 16A

Sample view of "Publisher Home" View on the HCN Administration Application

Healthcare Collaboration Network
File  Edit  View  Favorites  Tools  Help
◀ Back ▶ ⊗ □ △ Search Address [_____]

hcn
National Healthcare Collaboration Network

- home
- contact us
- legal
- help
- log out

IBM

Welcome:  Publisher  [Switch Role to Subscriber]

| Publications | Publication Requests | Authorization Requests | Health Topics | HCN Notifications | Participants |

HCN Notifications
Click on a subject title to view the Notification Details.

| Date | Time | Type | From | Subject |
|---|---|---|---|---|
| 2004-03-16 | 15:31 | Email | admin@hcn.com | test |
| 2004-03-04 | 16:10 | Email | admin@hcn.com | UI Spec 2 |
| 2004-03-04 | 16:09 | Email | admin@hcn.com | UI Spec 1 |

→ more HCN notifications

Publication Requests
The following table lists subscriber requests for publications

| Topic Name | Requesting Organization |
|---|---|
| ADR for Felbatol | Food and Drug Administration |
| ADR for Thalidomide | Centers for Disease Control and P |
| ADR for Arava | Centers for Disease Control and P |
| Plaque Diagnosis | Centers for Disease Control and P |
| Stroke Diagnosis | Centers for Disease Control and P |

→ more publication requests

Authorization Requests
No requests pending.

→ more authorization requests

Publications
Display Publications:
● All publications
○ Containing the word: [_____] [Display]  [Create Publication]

→ more publications

HCN Publication Logs
No log files found.

→ more publication logs

Health Topics
Display Topics:
● All topics
○ Containing the word: [_____] [Display]  [Create Topic]

→ more health topics

Participants
Display Participants:
● All participants
○ With names containing: [_____] [Display]

→ more participants home | contact us | legal | help | log out

Internet

System for Monitoring and Alerting of Adverse Drug Events in Near-Realtime

System for Monitoring and Alerting of Disease/Exposures in Near-realtime Using ME

PUBLISHER GATEWAY SYSTEMS FOR COLLABORATIVE DATA EXCHANGE, COLLECTION, MONITORING AND/OR ALERTING

PRIORITY CLAIM

The present application is a continuation of U.S. patent application Ser. No. 11/032,664 filed on Jan. 10, 2005 now abandoned and titled "Publisher Gateway Systems For Collaborative Data Exchange, Collection, Monitoring And/Or Alerting." The contents of which is incorporated herein by reference in its entirety.

CROSS-REFERENCE TO RELATED APPLICATIONS

There are three co-pending co-assigned related applications filed concurrently with the instant application Ser. Nos. 11/032,590, 11/032,405, and 11/032,391 the three co-pending and co-assigned applications are identified by the contents of which are hereby incorporated by reference as if recited in full herein.

RESERVATION OF COPYRIGHT

A portion of the disclosure of this patent document contains material to which a claim of copyright protection is made. The copyright owner has no objection to the facsimile or reproduction by anyone of the patent document or the patent disclosure, as it appears in the Patent and Trademark Office patent file or records, but reserves all other rights whatsoever.

BACKGROUND OF THE INVENTION

The present invention relates to data sharing using a computer network and may be particularly suitable for healthcare clinical data sharing over an intranet and/or the public Internet.

Healthcare communication systems are typically limited and generally non-standard between institutions and it is difficult to access, track, monitor and/or alert healthcare data across multiple healthcare providers. In the United States, there are over six thousand hospitals, hundreds of thousands of health professionals, and multiple other parties that may desire to exchange clinical data. There are technical, legal and/or societal obstacles for data sharing utilizing centralized data repositories to facilitate the data exchange, and it would be nearly impossible to maintain current awareness and/or access to central data repositories, even if such repositories existed. Further, many privacy organizations oppose a national (or multi-national or global) repository that collects patient information from patients being treated in a healthcare system.

In the past, conventional approaches for exchanging healthcare data included manual transmission of data such as mailing, telephone calls, exchange of data tapes, disks or files in project-specific formats and/or point-to-point interfaces, and/or to use data mining techniques to provide data sharing. That is, some conventional systems have been configured to share diverse data sets and distill information on specific events by Extracting data from the source, Transforming and normalizing the data, then Loading the transformed data into a central repository for data mining ("ETL"). Unfortunately, ETL can make such systems hard to use and may limit the scalability thereof.

BRIEF SUMMARY OF THE INVENTION

Particular embodiments are directed to Publisher sources of healthcare data configured to communicate with an Internet-based data sharing system. The Publisher includes a Publisher Gateway configured to: (a) receive patient data from a plurality of data input sources electronically; (b) automatically correlate data from the plurality of input sources associated with respective patients into respective electronic patient data records having electronically searchable data fields; and (c) electronically store the patient data records in a Publisher database Some embodiments are directed to methods of receiving and publishing source data from Publishers of source data to one or more participating Subscribers using a computer network. The methods include: (a) receiving data from a plurality of different data sources of disparate electronic data formats at a respective Publisher Gateway; (b) automatically electronically correlating related data from the data sources to generate at least one of person and/or event related electronic data records; and (c) automatically selectively publishing data from the electronic data records from respective Publisher Gateway to Subscribers over the computer network.

Yet other embodiments are directed to computer program products for providing a collaborative healthcare data sharing system using a computer network, the computer program product includes: a computer readable storage medium having computer readable program code embodied in the medium. The computer-readable program code including: (a) computer readable program code configured to receive and correlate data from a plurality of different data sources and place data related to a particular patient into a respective electronic patient data record having a plurality of electronically searchable data fields.

Some embodiments are directed to systems for collecting and forming electronically searchable electronic patient data records. The systems include a Publisher Gateway in communication with a plurality of participating Subscribers via a Message Flow Server and an Administrative Server. The Publisher Gateway is configured to receive data from a plurality of Publisher specific sources and correlate the data into an electronically searchable record of related data.

It is noted that embodiments and/or features described with respect to a particular type of implementation can be implemented in other ways, such as, for example, where embodiments are described as methods those features can be implemented as computer program products and/or devices or systems. These and other objects and/or aspects of the present invention are explained in detail in the specification set forth below.

BRIEF DESCRIPTION OF THE SEVERAL VIEWS OF THE DRAWINGS

FIG. 1D is a schematic illustration of the system shown in FIG. 1A illustrating that data can be input to a Publisher Gateway at an originating source Publisher and that publications (in different output formats or destinations) can be transmitted back to entities within or associated with the originating Publisher according to embodiments of the present invention.

FIG. 11C is a flow chart of operations that a Publisher can carry out to collect and/or correlate electronically searchable event records according to embodiments of the present invention.

FIG. 11D is a flow chart of operations that a Publisher can carry out in response to a Subscriber request for specified data according to embodiments of the present invention.

FIG. 13 is a sample message that includes diverse data records for a patient according to embodiments of the present invention.

FIG. 14 is a screen printout of an exemplary computer network (typically the web) portal for a Publisher according to embodiments of the present invention.

FIG. 15 is a screen printout of an exemplary topic catalog accessible via a computer network portal according to embodiments of the present invention.

FIGS. 16A and 16B are screen printouts of an exemplary Publisher "home" view from/on an administration application according to embodiments of the present invention.

DETAILED DESCRIPTION OF THE INVENTION

Figure 1A:
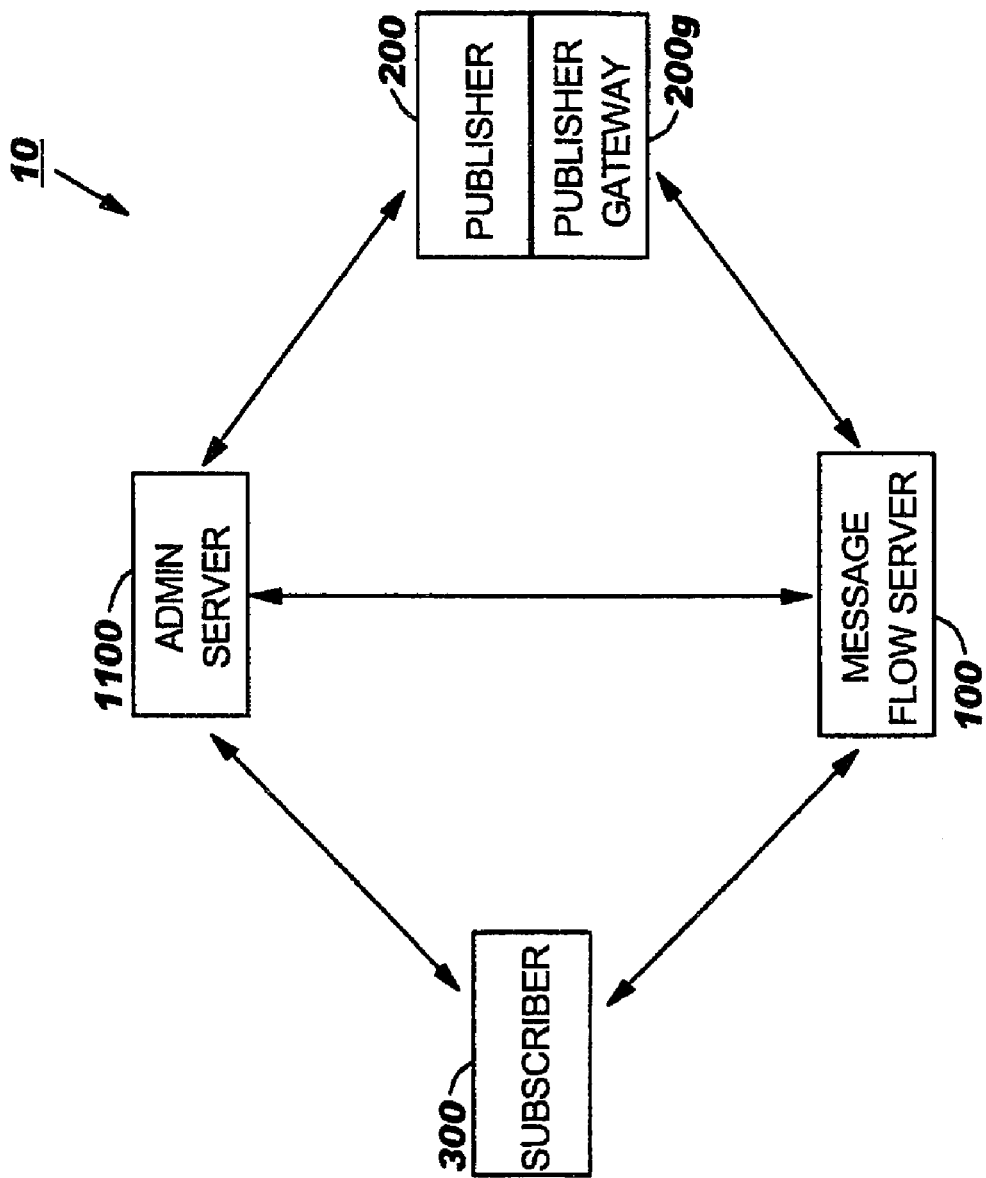
FIG. 1A is a schematic illustration of a computer networked system used to provide collaborative data exchange according to embodiments of the present invention.

The present invention will now be described more fully hereinafter with reference to the accompanying figures, in which embodiments of the invention are shown. This invention may, however, be embodied in many different forms and should not be construed as limited to the embodiments set forth herein. Like numbers refer to like elements throughout. In the figures, certain layers, components or features may be exaggerated for clarity, and broken lines illustrate optional features or operations unless specified otherwise. In addition, the sequence of operations (or steps) is not limited to the order presented in the claims or figures unless specifically indicated otherwise. Where used, the terms "attached", "connected", "contacting", "coupling" and the like, can mean either directly or indirectly, unless stated otherwise. As used herein, the term "and/or" includes any and all combinations of one or more of the associated listed items.

It will be understood that, although the terms first, second, etc. may be used herein to describe various elements, these elements should not be limited by these terms. These terms are only used to distinguish one element from another element. Thus, a first element discussed below could be termed a second element without departing from the scope of the present invention.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein.

The term "Publisher" means a participant that can provide or "publish" data to an external and/or internal site using a computer network. The Publisher is typically an original data source. The term "Subscriber" means a participant that can request topical data using a computer network. Publishers can also be Subscribers to their own data or to other Publishers' data. The term "automatic" means that substantially all or all of the operations so described can be carried out without the assistance and/or manual input of a human operator. The term "electronic" means that the system, operation or device can communicate using any suitable electronic media and typically employs programmatically controlling the communication between participants using a computer network. The term "hub" means a node and/or control site (or sites) that controls data exchange between Publishers and Subscribers using a computer network. The hub may not be required for a Publisher site to access its own messages (i.e., where the healthcare data request is from a Subscriber within the Publisher institution and is only for institution specific data, typically controlled by the Publisher Gateway, from the Publisher institution). The term "HIPAA" refers to the United States laws defined by the Health Insurance Portability and Accountability Act. The term "open standard(s)" refers to standardized electronic formats of data using standards that are open to the public (i.e., non-proprietary). Examples of current open-standard messaging formats include HL-7, MAGE-ML, and relevant industry standard codes presently existing or yet to be developed. For example, for healthcare applications, industry standard codes can include, but are not limited to those used for diagnosis (ICD-9, ICD-10), procedures (CPT), lab results (LOINC and/or SNOMED) and drugs (NDC, RxNorm).

The term "message" means one or more data elements for a topic that can be in a defined computer code language format. There can be different message types, such as, but not limited to, command and control messages, clinical or target data publication messages, notification messages, and alert messages. The messages can include elements received from Publisher-specific internal IT computer systems, typically HL7 message formats. The publication of target data can be carried out as a topic publication message that can be transmitted to a Subscriber by way of their respective gateways. The topic publication message can include a content definition header, which can be in a different format from other data elements in the topic publication message (such as in XML). Typically, the data to be transmitted with the header is enclosed in the body of the message (called an envelope or enclosure), and what resides in the envelope can generally be data in any arbitrary industry specific format. The other data elements in the topic publication message can be in industry specific format and/or code or mapped to a defined standardized message code/content for a defined communication protocol/common language between all participants. For example, for healthcare data sharing systems, the topic publication message can include a content definition summary/header and include those clinical data elements associated with a Subscriber's data request. The message data elements can be configured to generate a (typically short) text summary of that data element.

Embodiments of the present invention may be particularly suitable for collaborative healthcare data sharing systems that one or more can be implemented using a computer network. The term "computer network" includes local area networks (LAN), wide area networks (WAN) and may, in certain embodiments, include a private intranet and/or the public Internet (also known as the World Wide Web or "the web"). The healthcare or other data sharing systems contemplated by embodiments of the present invention may be implemented as one or more of a state system, a regional system, a national system and/or a multi-national system.

The terms "healthcare data" and "clinical data" are used interchangeably and include any and/or all of a treatment, medicinal, drug or prescription use, laboratory tests and/or results, diagnostic information, demographic information, a physical location, a home address (such as a zip code) or travel or other relevant data associated with an event or patient. The healthcare data can be used for clinical trials, adverse drug events, disease surveillance (such as for infection containment or alert) or other bio-surveillance and/or quality of care evaluations. Embodiments of the present invention can also be used for non-healthcare systems. The non-healthcare systems can be configured to provide systems for application-specific data. Thus, for clarity of discussion, the present invention will be primarily discussed herein with respect to healthcare systems, but the features, components and/or operations are not limited thereto.

It is also noted that embodiments of the invention may be discussed with respect to IBM specific products for completeness of discussion. However, the invention is not limited thereto as other products and/or suppliers may be used to implement the invention.

As will be appreciated by one of skill in the art, embodiments of the invention may be embodied as a method, system, data processing system, or computer program product. Accordingly, the present invention may take the form of an entirely software embodiment or an embodiment combining software and hardware aspects, all generally referred to herein as a "circuit" or "module." Furthermore, the present invention may take the form of a computer program product on a computer-usable storage medium having computer-usable program code embodied in the medium. Any suitable computer readable medium may be utilized including hard disks, CD-ROMs, optical storage devices, a transmission media such as those supporting the Internet or an intranet, or magnetic or other electronic storage devices.

Computer program code for carrying out operations of the present invention may be written in an object oriented programming language such as Java, Smalltalk or C++. However, the computer program code for carrying out operations of the present invention may also be written in conventional procedural programming languages, such as the "C" programming language or in a visually oriented programming environment, such as VisualBasic.

Certain of the program code may execute entirely on one or more of the user's computer, partly on the user's computer, as a stand-alone software package, partly on the user's computer and partly on a remote computer or entirely on the remote computer. In the latter scenario, the remote computer may be connected to the user's computer through a local area network (LAN) or a wide area network (WAN), or the connection may be made to an external computer (for example, through the Internet using an Internet Service Provider). As will be discussed further below, typically, some program code executes on each Publisher Gateway computer and some program code executes on a hub server (such as a Message Flow Server and/or a web application or Administrative Server) with communication between the gateways and the hub server using the Internet.

The invention is described in part below with reference to flowchart illustrations and/or block diagrams of methods, systems, computer program products and data and/or system architecture structures according to embodiments of the invention. It will be understood that each block of the illustrations, and/or combinations of blocks, can be implemented by computer program instructions. These computer program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the block or blocks.

These computer program instructions may also be stored in a computer-readable memory or storage that can direct a computer or other programmable data processing apparatus to function in a particular manner, such that the instructions stored in the computer-readable memory or storage produce an article of manufacture including instruction means which implement the function/act specified in the block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions/acts specified in the block or blocks.

Embodiments of the present invention will now be discussed with respect to the figures. FIG. 1A illustrates an exemplary electronic collaborative data sharing system 10 that includes a Message Flow Server 100 in communication with an Administrative Server 1100. As shown, the system also includes participant Publishers 200 and Subscribers 300 (shown as one of each for ease of discussion). The Administrative Server 1100 can be configured to control participant access and communicate with the Message Flow Server 100 so that only Publisher-approved publications are transmitted or routed to Subscribers responsive to Publisher input. The function of all or some of the Administrative Server 1100 can be incorporated into the Message Flow Server 100. Typically, however, the Administrative Server 1100 is separate from the Message Flow Server 100 and communicates electronically therewith. Similarly, although shown as two servers, more than two servers can be used to carry out either the Message Flow Server or Administrative Server functions. It will be appreciated by those skilled in the art that the functions can be combined in a single physical node.

Each Publisher 200 can include at least one Publisher Gateway 200g. The Publisher Gateway 200g communicates with the Message Flow Server 100 to transmit (their internally authorized) publication data to Subscribers 300. The Publisher 200 typically includes a private intranet of affiliated departments (such as admission and/or discharge), physicians, laboratories, and pharmacies as will be discussed further below. The gateway 200g is configured to collect clinical data from a respective Publisher 200. In some embodiments, the gateway 200g is configured to collect only temporal data, based on the size of the storage media.

The Subscriber 300 can receive approved clinical publication data from participating Publishers 200 by any suitable communication means, including one or more of wireless messaging to PDA's, wireless communication systems (such as cellular telephones), personal or business computers, portable computers, via email (with or without attachments), voicemail, storage into a database or storage medium associated with the Subscriber, a Subscriber Gateway (300g, FIG. 6) and the like. The publication data can be provided as a clinical topic publication message in a format that a Subscriber 300 can select. The Subscriber 300 can request different publication formats or destinations for different publication data. The destination may be established during site installation or configuration set-up or may be effectuated by the Administrative Server 1100 at start-up or in response to a change request. In some embodiments, the conditions or rules for publication, subscription, destination and data format can be controlled/established using the Administrative Server 1100.

Figure 1B:
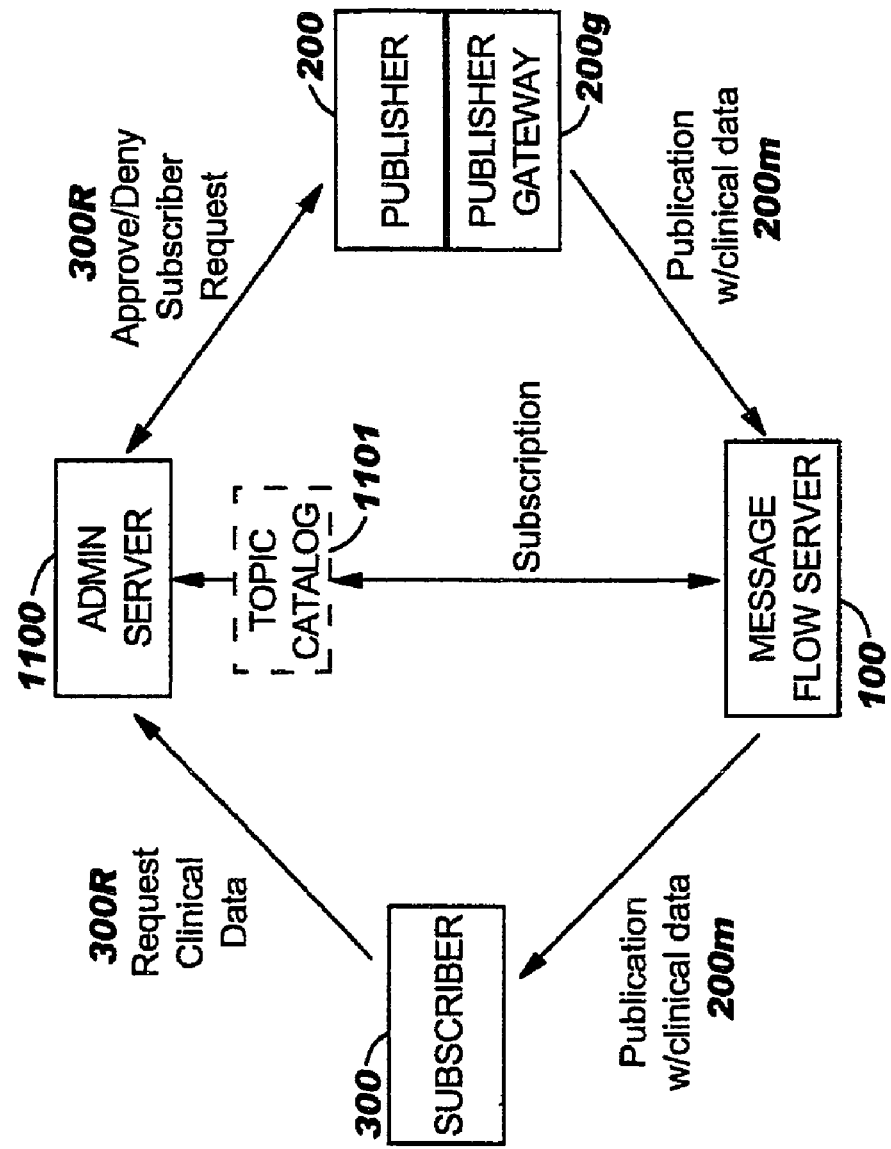
FIG. 1B is a schematic illustration of the system shown in FIG. 1A illustrating an exemplary publication cycle according to embodiments of the present invention.

As shown in FIG. 1B, the system 10 can include a topic catalog of different data types or content, that may have different publication rules, that may be of interest. The electronic topic catalog 1101 can be a global topic catalog 1101 that is displayed by the Administrative Server 1100 to the Subscribers and Publishers 300, 200. A Subscriber 300 can select a topic of interest from the topic catalog 1101 or create a new topic if the existing topics do not have the desired content, format, and/or security level. The desired message format may be requested by creating or selecting a topic with a content-constraint that selects the desired format. That is, within the topic catalog, two different topics may have the same data content but be different topic entries in the topic catalog based on the desired output format and/or communication mode, dictating how the requested data is transmitted to them.

Still referring to FIG. 1B, an exemplary publication cycle is shown. A Subscriber 300 accesses the system at a portal hosted by the Administrative Server 1100 and enters a request for clinical data 300R. The Administrative Server 1100 can forward a Subscriber request for publication 300R to a Publisher 200 using the system portal (Administrative Server Web Application). Typically, the request is approved or denied upon review by a person (rather than electronically) by each respective Publisher 200. The request for a particular Subscriber and topic may be approved once. Typically, the Administrative Server 1100 sends a request notification and the Publisher responds to the request notification using the Administrative Server web application. Hence, in operation, the request notification message and request response (as well as the Subscriber notification regarding same) can electronically travel to and from Subscribers/Publishers through the Administrative Server.

In some particular embodiments, one or more Publishers 200 can be configured with electronic filters or constraints that can automatically electronically approve or deny the publication requests for some or all of the topics. In addition, in some embodiments, a Publisher 200 can pre-identify to the Administrative Server 1100 those Subscribers that they have a standing "deny" for (whether by topic or identity of the Subscriber). In such a situation, the Administrative Server 1100 can be configured to not send Requests for publication from the identified "blacklist" Subscriber and/or "topic".

Once a Publisher 200 approves a publication request 300R for a particular Subscriber 300, any ongoing clinical data collected or aggregated for a patient in their gateway that meets that topic (content definition) request 300R can be published to the Message Flow Server 100 as a publication 200m which is then automatically forwarded to the requesting and approved Subscriber 300. This can be described as a Publisher-specific approved subscription for a particular topic with defined data content to a particular Subscriber. For a particular Publisher publication transmitted by a respective Publisher 200, there can be many approved Subscribers having approved subscriptions. When a Publisher 200 transmits a publication with topical data 200m to the Message Flow Server 100, it can be "broadcast" to multiple approved Subscribers 300 generally concurrently. To cancel a subscription, a respective Publisher 200 can access the system portal of the Administrative Server 1100 and transmit a subscription cancellation order for one or more Subscribers and/or for a particular topic. This will prevent future publication transmissions (for a selected topic or topics or all topics) from that Publisher 200 from being sent automatically to that Subscriber 300.

Figure 1C:
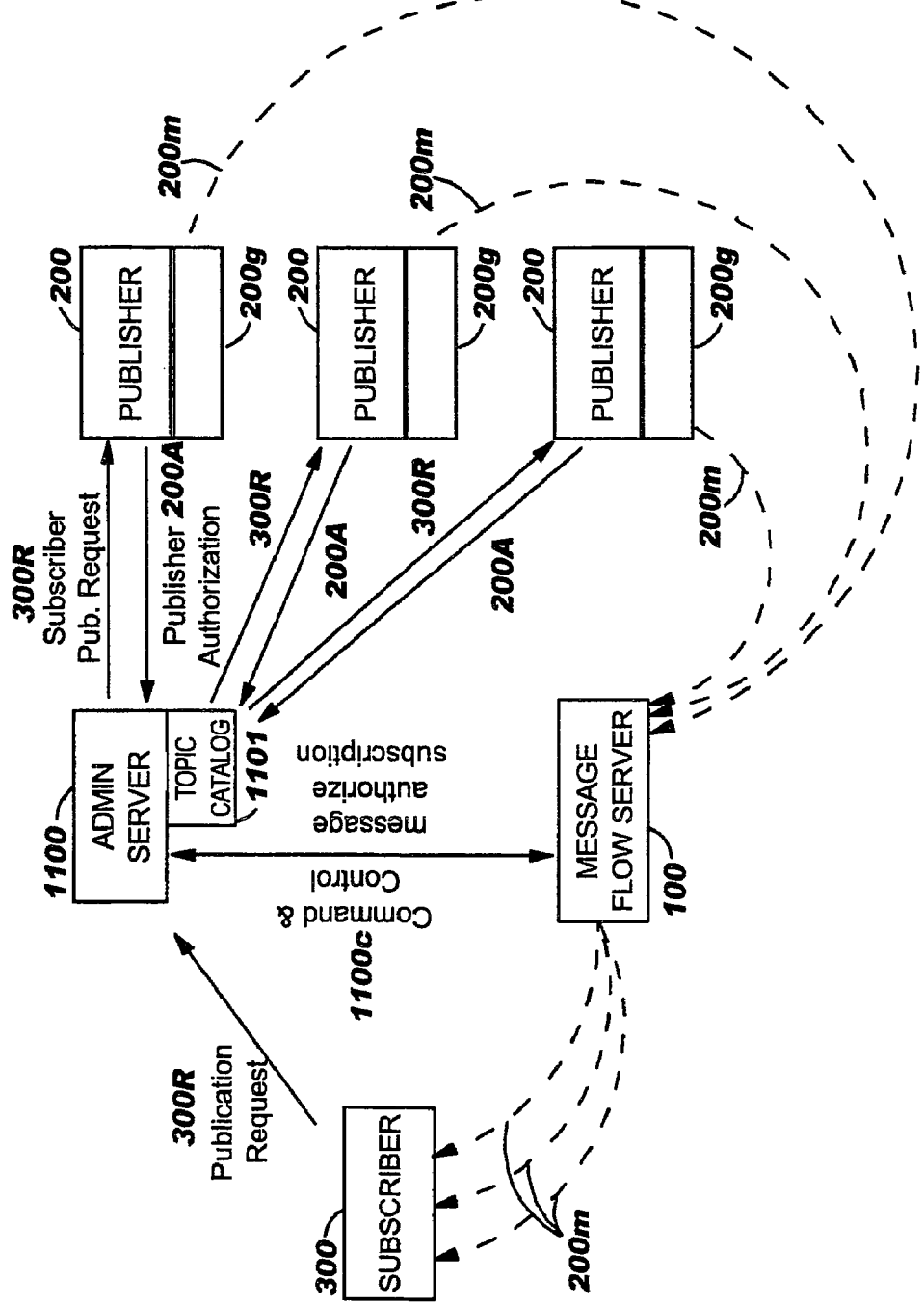
FIG. 1C is a schematic illustration of the system shown in FIG. 1A illustrating an exemplary publication cycle of a selected Subscriber topic and between a Subscriber and a plurality of different Publishers according to embodiments of the present invention.

FIG. 1C illustrates that the communications between the participants 200, 300 and servers, 1100, 100 can be message-based communications. As shown, the Subscriber 300 can select (or create) a request for publication of a particular topic 300R from the topic catalog 1101. This generates a notification of a publication topic request 300R that the Administrative Server 1101 can display on the Publisher screen of the system portal. The publication topic request 300R will define a topic title or name (which has an associated topic description) for the relevant clinical data of interest and identify the requesting Subscriber. The Publisher 200 responds to request for publication by approving or denying the request and sending a message to the Administrative Server 1100. As shown, each Publisher 200 sends an approval response 200a to the Administrative Server 1100. If approved, the Administrative Server 1100 sends a command and control message 1100c to the Message Flow Server 100 to notify the Message Flow Server 100 that a Subscriber 300 has an approved subscription and is entitled to receive publication messages 200m sent from a particular Publisher for that approved topic. As shown, for a single publication topic request from a Subscriber 300, the Message Flow Server 100 can receive and transmit many topic publication messages of clinical data 200m from different Publishers 200.

Figure 7:
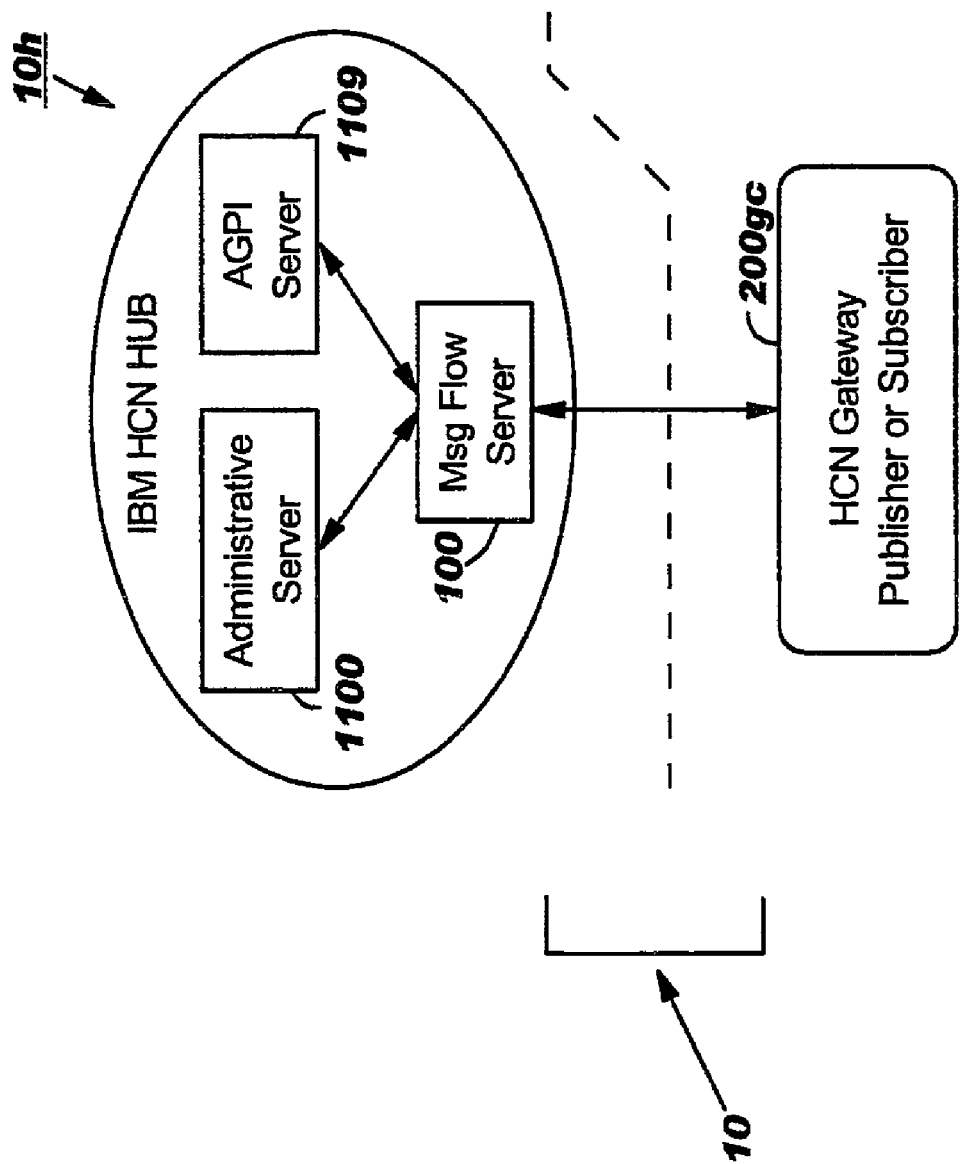
FIG. 7 is a schematic illustration of components of a hub according to embodiments of the present invention.

One or more of the Publisher Gateways 200g can also be configured as a Subscriber Gateway 300g to be a common gateway 200gc for both functions to thereby accept external data as a Subscriber and to transmit internal data as a Publisher as shown in FIG. 7. In other embodiments, a Subscriber 300 can communicate without the use of a Subscriber Gateway 300g as noted above, or a Subscriber 300 can have a dedicated Subscriber Gateway 300g.

Figure 6:
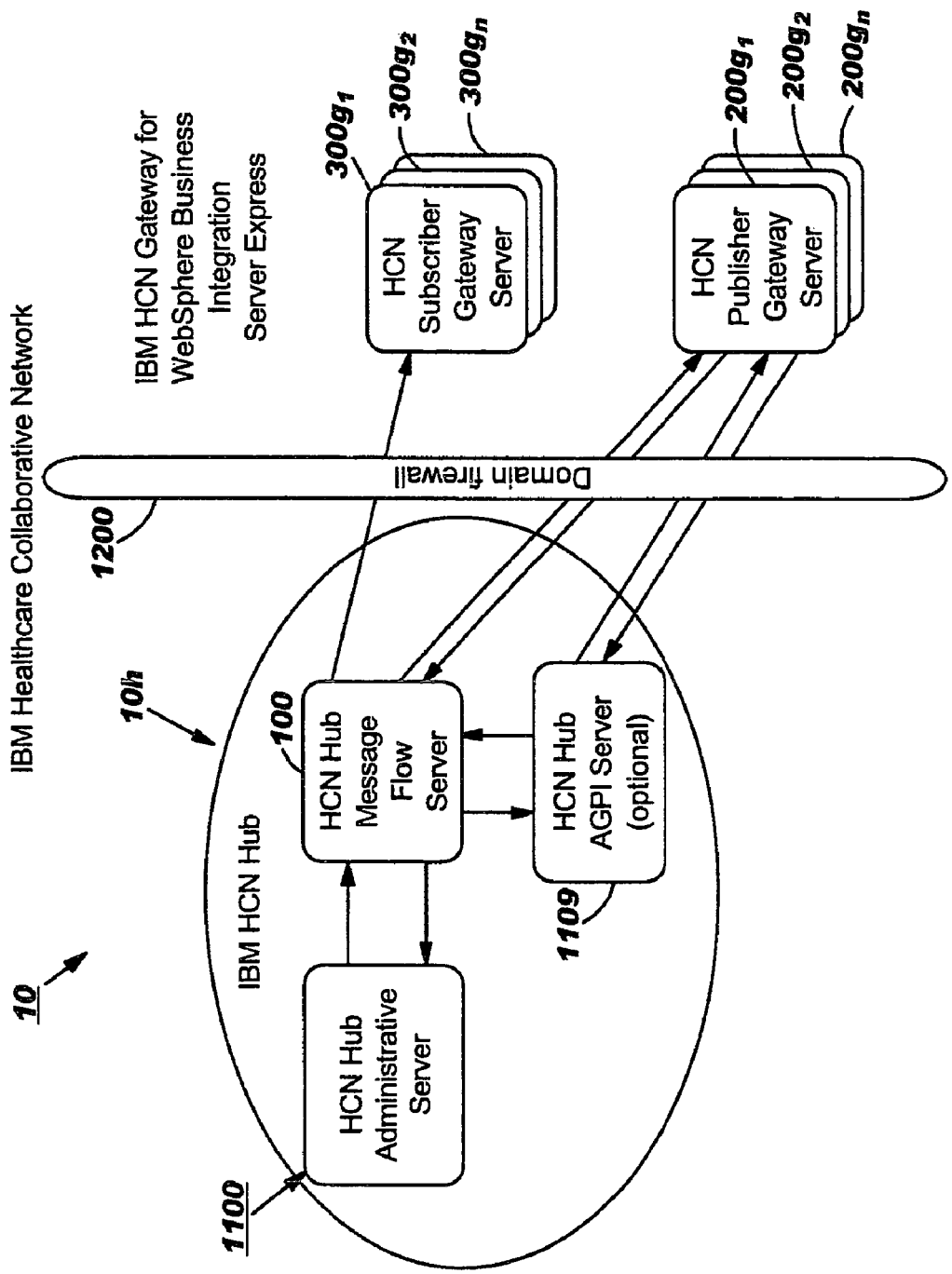
FIG. 6 is a schematic illustration of a collaborative computer network system according to embodiments of the present invention.

FIG. 1D illustrates that some Subscribers 300 can be affiliated with the Publisher 200. The Message Flow Server 100 can transmit or route selected clinical data to the Subscribers 300 within the Publisher's organization (as well as to external Subscribers). The Message Flow Server 100 can communicate with the Subscribers 300 through the Publisher Gateway 200g, with the Publisher Gateway 200 configured to have dual modality operation/function to thereby also act as a Subscriber Gateway 300g thereby utilizing a common Subscriber/Publisher Gateway 200gc (FIG. 7) or through a separate Subscriber Gateway 300g (FIG. 6). In other embodiments, the Message Flow Server 100 can transmit the clinical data and/or requested information directly to the Subscribers 300 using their elected electronic communication modality as discussed above. The Subscribers 300 can include administrators, physicians, department heads, or other functions or persons desiring clinical data. As noted before, the clinical data can be transmitted to the Subscriber in one or more formats, including, but not limited to, email, download or transmission to a database or electronic storage medium, pages, text or voice messaging via telephone or wireless communication devices including cellular phones and PDA's or other portable and/or pervasive computing devices. For example, a clinician can subscribe to receive clinical data from their own healthcare institution that notifies him or her of cardio patients (or other healthcare department or specialty) exhibiting certain symptoms or selected criteria such as a prescribed medication.

This information can be sent in any suitable format, such as to a portable communications device to allow for more prompt notification and allow for any care follow-up as desired. In another example, an administrator can request clinical data for all patients having a hospital stay that is over a defined threshold for various diagnosis or other criteria for healthcare standard of care monitoring reports. In yet another example, the department head may subscribe to a topic for publication messages from his or her respective care facility that includes, for example, notification of patients treated by physicians within his or her department that were prescribed a certain medication or not prescribed a certain medication for particular symptoms, lab work and/or diagnosis. This may identify training needs or patient follow-up.

The system 10 can include large numbers of participant Subscribers and Publishers. Although shown in the figures as a single Message Flow Server 100, at a single node, a plurality of such servers and/or nodes may be used as appropriate for redundancy and/or service.

For healthcare applications, one class of Publishers of data are typically care providers such as hospitals, clinics, nursing homes, rehabilitation centers, urgent care facilities, laboratories, physicians and other care providers, particularly those providers that are under an obligation to report clinical data to regulatory agencies. Other classes of Publishers can include independent laboratories, pharmacy benefit managers, and other clinical repositories.

Typical Subscribers include federal, state and/or local (local to a Publisher site) regulatory and/or governmental agencies, any public health agency, clinics or hospitals (which may also be Publishers), insurers, pharmaceutical companies, researchers, public health and/or policy institutions/agencies, and the like. The system 10 can be used as part of a National Health Information Infrastructure (NHII) and/or Regional or State Health Information Organization(s).

In some embodiments, a third category of participant, which may be described as an observer, may optionally be present. An observer may have standard monitoring protocols established, by which the observer can obtain copies of clinical data, data messages and/or summaries of messages sent to and/or from certain or all Publishers 200 and/or certain and/or all Subscribers 300. In addition, there may be a fourth administrative category participant for the hosting service (not shown).

For Internet based applications, the Message Flow Server 100, Subscribers 300, Publishers 200 and/or associated gateways 200g, 300g can be configured to operate using SSL (Secure Sockets Layers) and a high level of encryption. The users or participants can be assigned to "organizations" which have a set of attributes that process data for their systems. The system 10 has a registry of user's that define the user's role and provide a specific level of authority, which is identified at the web portal (such as upon sign on). The Publishers 200 and Subscribers 300 communicate with the hub 10h via the web portal 10p (FIGS. 6, 8) and Administrative Server 1101 to publish clinical data from one or more Publishers 200 on topics to interested Subscribers 300 via the Message Flow Server 100 that is controlled by the Administrative Server 1100.

Figure 2:
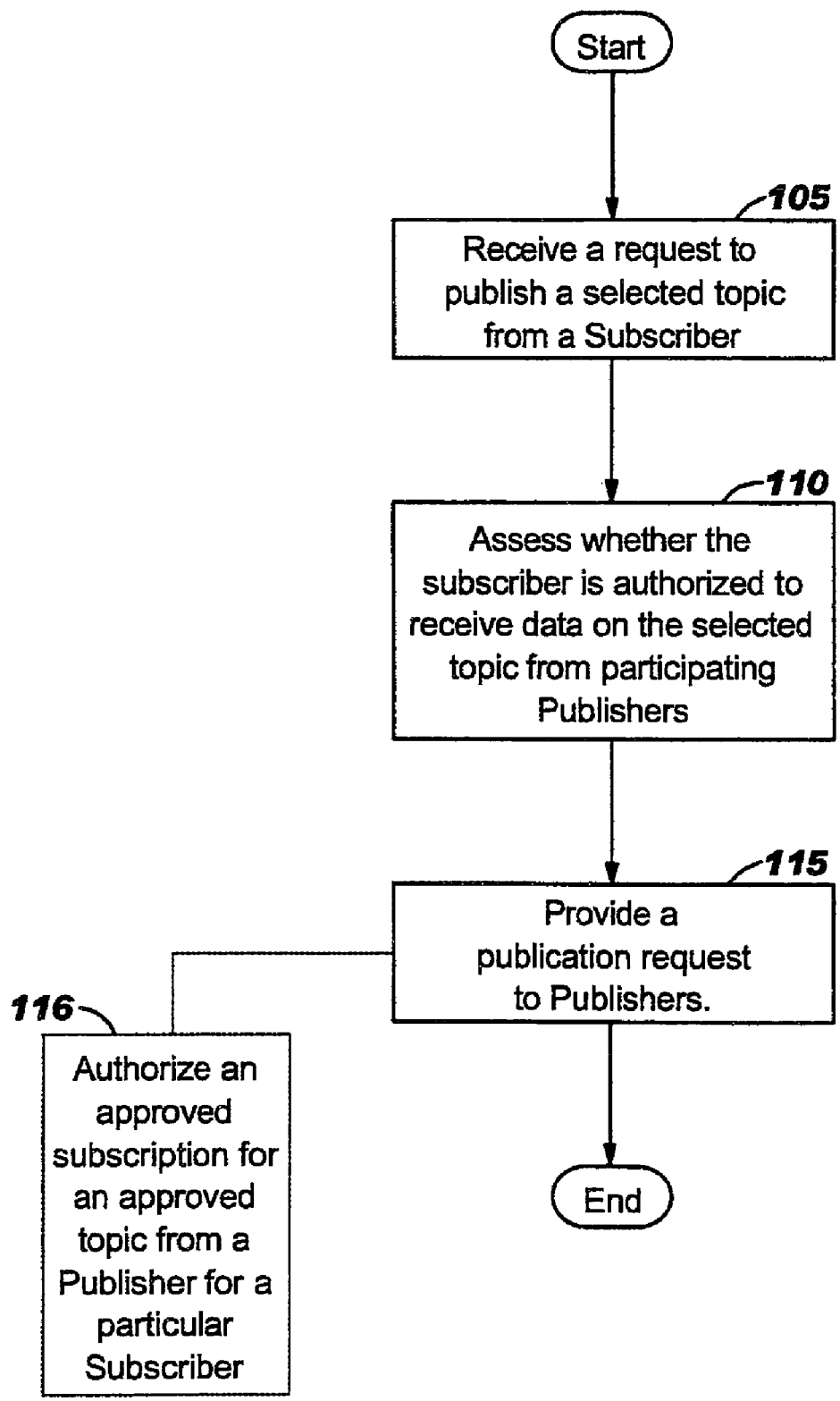
FIG. 2 is a flow chart of exemplary operations that can be used to carry out certain embodiments of the present invention.

FIG. 2 illustrates operations that can facilitate collaborative sharing of data using an Administrative Server 1100 and a Message Flow Server 100 according to embodiments of the present invention. As shown, a request to publish a selected topic is received by the Administrative Server (block 105). The Administrative Server can assess whether the Subscriber is authorized to receive data from participating Publishers (such as from any, all or only selected Publishers) (block 110). The publication request can be forwarded to Publishers so that each Publisher can approve or deny the publication request for a particular topic or Subscriber (block 115). In particular embodiments, the Subscriber topic request may be pre-screened by the Administrative Server to see if any "blacklist" or standing instruction exists from a particular Publisher for a particular Subscriber or topic. If a Publisher approves the publication request for a particular topic from a particular Subscriber an authorized standing subscription order can be established, allowing clinical data to be automatically sent from the approving Publisher to the authorized requesting Subscriber via the Message Flow Server 100 (block 116). The Administrative Server 1100 can transmit a subscription message to the Message Flow Server to initiate the subscription and allow clinical data to be routed from the Publisher to the Subscriber via the Message Flow Server without requiring the requestor to request publication for future events or data on that topic from that Subscriber.

Figure 3:
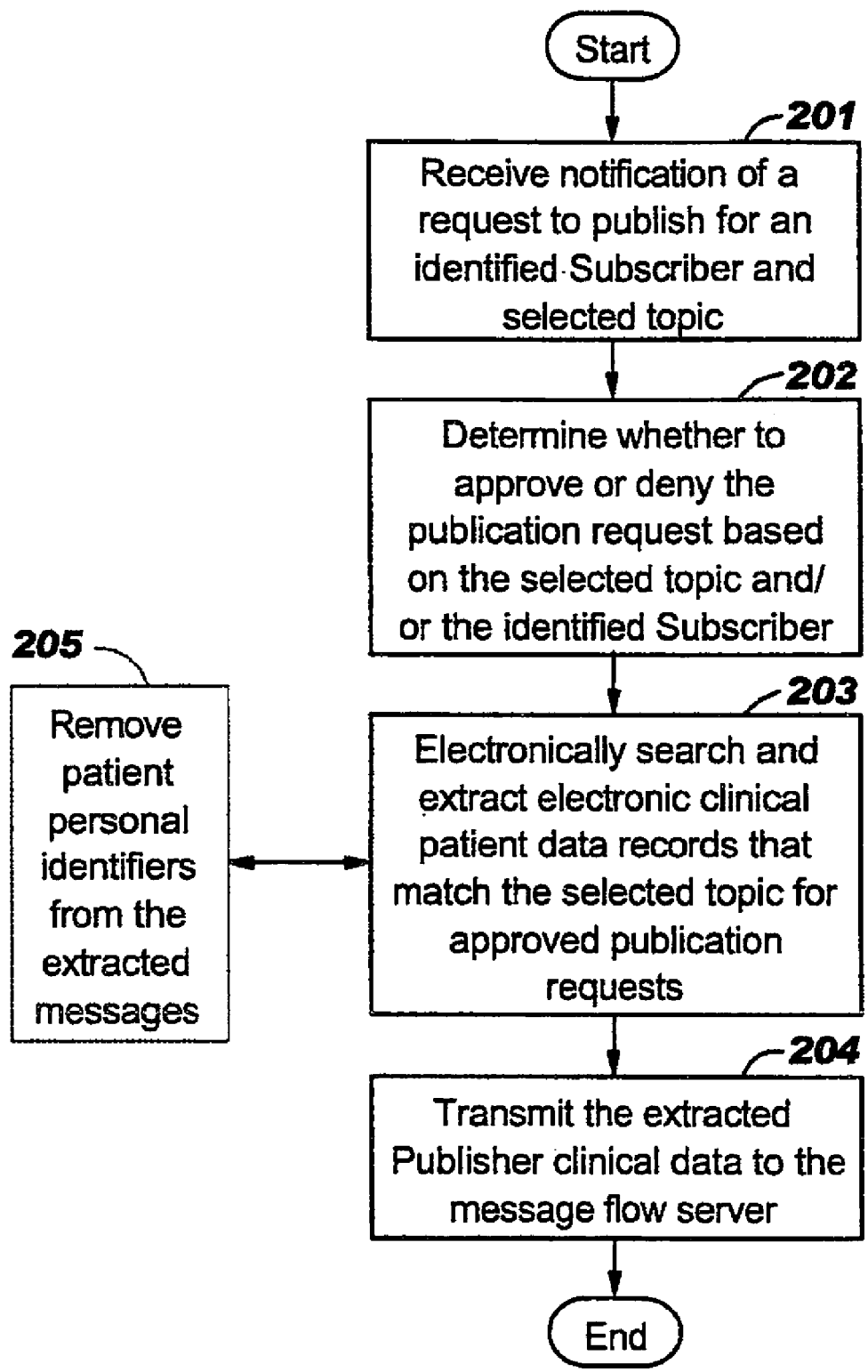
FIG. 3 is a flow chart of other exemplary operations that can be used to carry out embodiments of the present invention.

FIG. 3 illustrates exemplary operations that can be carried out by a Publisher 200. As shown, a notification of a request to publish is received at the Publisher portal (the Administrative Server application) for an identified Subscriber and topic (block 201). The notification can be on any viewing screen, but is typically in the "inbox" of the Publishers. The Publishers can each determine whether to approve or deny the publication request for a respective Subscriber and/or topic request. The Publishers can review the notification and respond to the web application portal an approval or denial based on Publisher specific preferences, criteria, rules and/or constraints (block 202). The Publisher approval and/or denial for the request can be selected on the web application portal and sent as a notification from the Administrative Server to the Subscriber. The notification may be viewed by the requesting Subscriber in an "inbox" of the Subscriber portal.

The Publisher Gateway can be in communication with a Publisher record database that stores electronic patient data records that have been aggregated and configured into standardized message data formats, typically open-standard message formats, to form electronic clinical data message records of patients. The Publisher Gateway 200g can use search and filter rules and/or logic associated with an approved topic to electronically query the (local) Publisher database and apply evaluation logic to identified data records to search and extract messages of patient record data that match the selected topic for approved publication requests (block 203). The extracted Publisher patient data messages can be transmitted to the Message Flow Server (block 204). In some embodiments, the patient data messages can be filtered to automatically and/or electronically to remove certain information, such as personal identifiers, prior to the transmission (block 205). The optional filtering can be used based on the rules of the Publisher (to comply with business or regulatory rules, such as HIPAA privacy rules or the like), and/or can be based on the identity of the Subscriber requesting the data and/or on the topic requested for publication.

The Publisher patient record database, which can be a patient message database, can be configured to include a finite time period of patient data messages, typically between about 1-six months, and more typically less than about three months, and even more typically between about 15-60 days, depending on the size of the storage media. The older patient record data maybe purged or transferred to one or more Publisher controlled history databases for subsequent use, such as for historical trend analysis as desired. In the periodically purging embodiment (typically a first-in, first-out (FIFO) based purging protocol), the system 10 acts as a temporal system that can provide relatively current clinical data. In some embodiments, the Publishers 200 can be configured to cache their respective data records so that data that is older (not marked as "recent", "in-use" or used recently, such as within the last 30-60 days) can automatically electronically "fall-off" the end of the cache time period (the cache period being typically limited by hardware storage limitations). The Subscribers 300 can have repositories that store or cache the messages into their own historical databases or systems. Thus, in some embodiments, there is no central repository of patient data. The Publisher Gateway 200g may also have other circuits or modules, such as a message cache that can suspend transmission of the extracted patient data message(s) pending receipt of additional patient data (aggregation of different inputs from labs, pharmacies, and the like) for a more complete response to a topic as will be discussed further below.

The publication request from a Subscriber 300 can be in the same standardized message format as the published patient data messages from the Publishers 200 (e.g., HL7). The publication of Publisher data messages can be an event-based operation whereby a publication can be generated in substantially real-time from when a patient record is identified as meeting the data content of an approved subscription topic to a Subscriber request for publication (typically in less than an hour, and in some embodiments in less than about 10 minutes). In other embodiments, the evaluation of data records may be performed at desired intervals on defined or in situ applied evaluation cycles.

Figure 4:
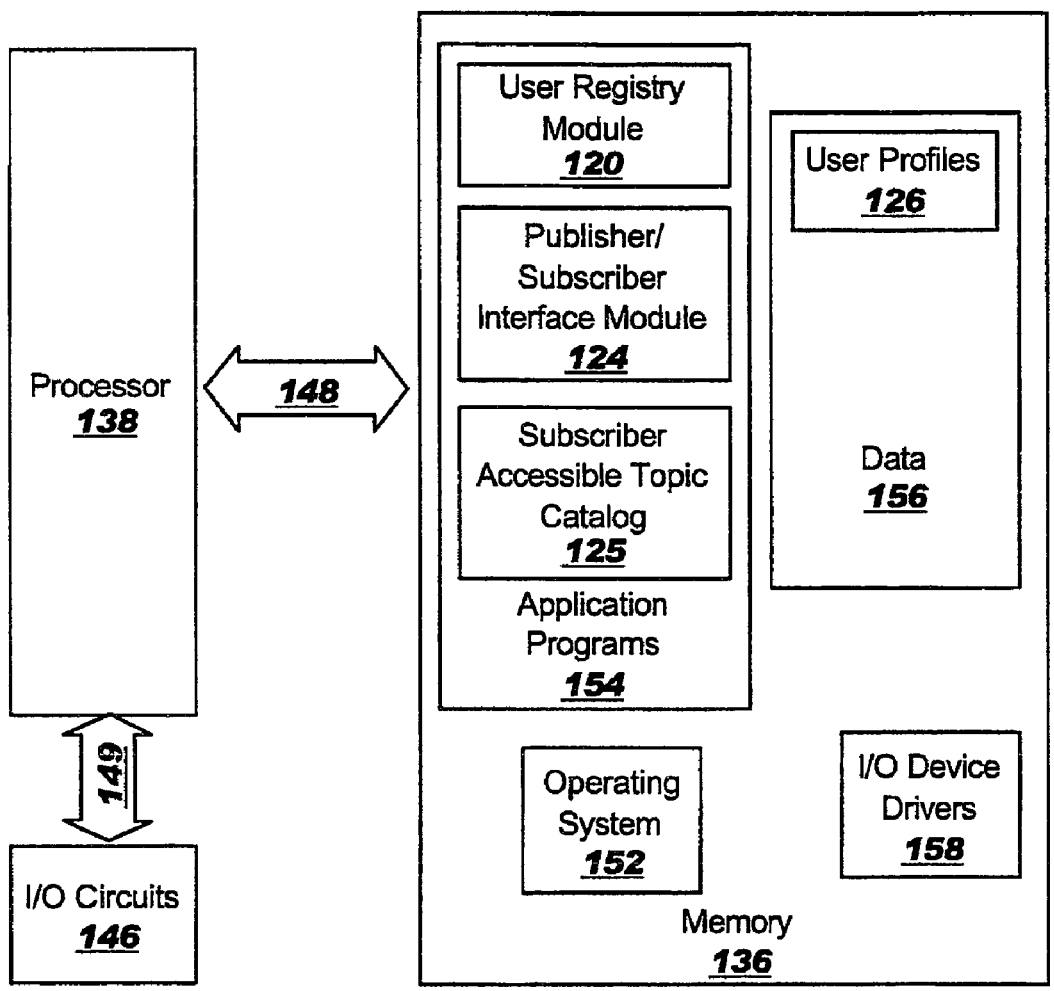
FIG. 4 is a block diagram of a data processing system according to embodiments of the present invention.
Figure 5:
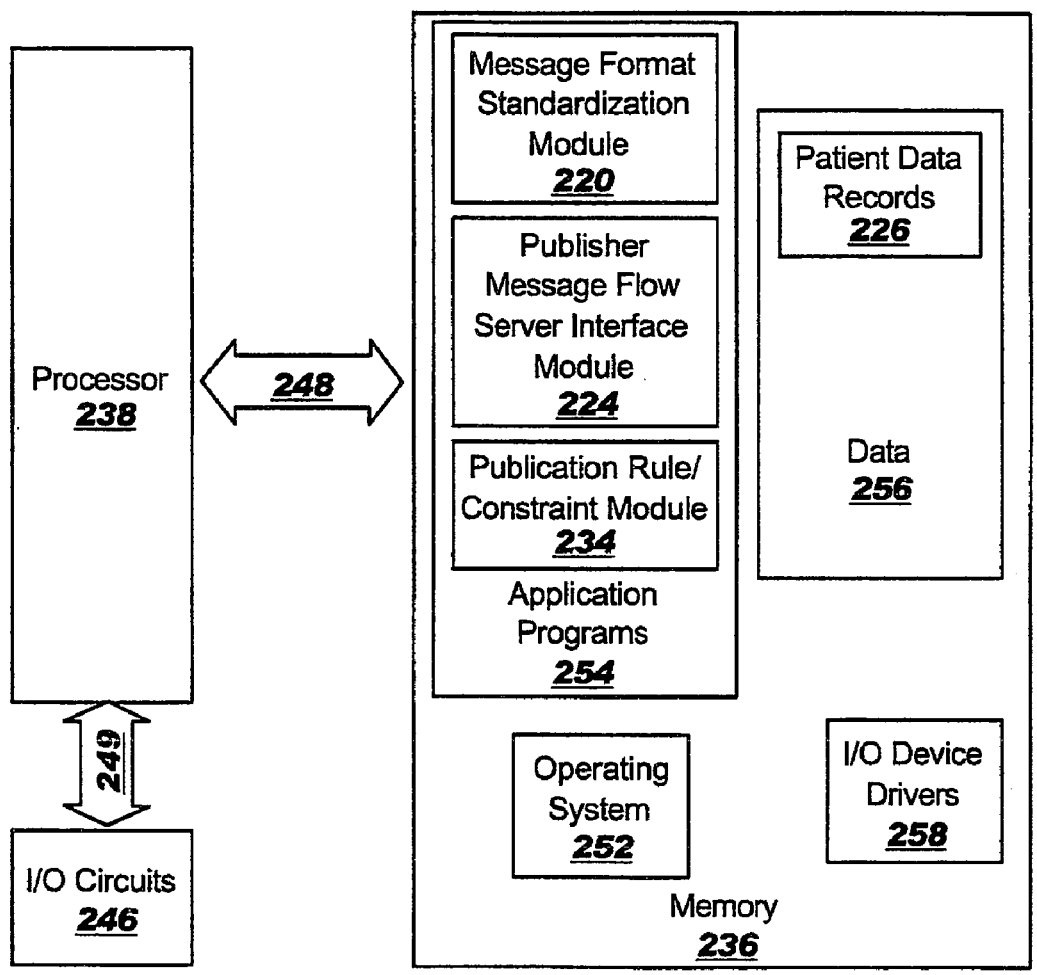
FIG. 5 is a block diagram of a data processing system according to embodiments of the present invention.

FIGS. 4 and 5 illustrate exemplary data processing systems or database environment that may be included in devices operating in accordance with some embodiments of the present invention. As illustrated in FIG. 4, a data processing system which can be used to carry out or direct operations of the hub and/or web application (Administrative Server) and/or Message Flow Server, includes a processor 138, a memory 136 and input/output circuits 146. The data processing system may be incorporated in, for example, one or more of a personal computer, server, router or the like. The processor 138 communicates with the memory 136 via an address/data bus 148 and communicates with the input/output circuits 146 via an address/data bus 149. The input/output circuits 146 can be used to transfer information between the memory (memory and/or storage media) 136 and another computer system or a network using, for example, an Internet protocol (IP) connection. These components may be conventional components such as those used in many conventional data processing systems, which may be configured to operate as described herein.

Similarly, FIG. 5 illustrates a data processing system which can be used to carry out and/or direct operations of the Publisher Gateway, includes a processor 238, a memory 236 and input/output circuits 246. The data processing system may be incorporated in, for example, one or more of a personal computer, server, router or the like. The processor 238 communicates with the memory 236 via an address/data bus 248 and communicates with the input/output circuits 246 via an address/data bus 249. The input/output circuits 246 can be used to transfer information between the memory (memory and/or storage media) 236 and another computer system or a network using, for example, an Internet protocol (IP) connection. These components may be conventional components such as those used in many conventional data processing systems, which may be configured to operate as described herein.

In particular, the processor 138, 238 can be commercially available or custom microprocessor, microcontroller, digital signal processor or the like. The memory 136, 236 may include any memory devices and/or storage media containing the software and data used to implement the functionality circuits or modules used in accordance with embodiments of the present invention. The memory 136, 236 can include, but is not limited to, the following types of devices: cache, ROM, PROM, EPROM, EEPROM, flash memory, SRAM, DRAM and magnetic disk. In some embodiments of the present invention, the memory 136, 236 may be a content addressable memory (CAM).

As further illustrated in FIGS. 4 and 5, the memory (and/or storage media) 136, 236 may include several categories of software and data used in the data processing systems: an operating system 152, 252; application programs 154, 254; input/output device drivers 158, 258; and data 156, 256. As will be appreciated by those of skill in the art, the operating system 152, 252 may be any operating system suitable for use with a data processing system, such as IBM®, OS/2®, AIX® or zOS® operating systems or Microsoft® Windows®95, Windows98, Windows2000 or WindowsXP operating systems Unix or Linux™. IBM, OS/2, AIX and zOS are trademarks of International Business Machines Corporation in the United States, other countries, or both while Linux is a trademark of Linus Torvalds in the United States, other countries, or both. Microsoft and Windows are trademarks of Microsoft Corporation in the United States, other countries, or both. The input/output device drivers 158, 258 typically include software routines accessed through the operating system 152, 252 by the application programs 154, 254 to communicate with devices such as the input/output circuits 146, 246 and certain memory 136, 236 components. The application programs 154, 254 are illustrative of the programs that implement the various features of the circuits and modules according to some embodiments of the present invention. Finally, the data 156, 256 represents the static and dynamic data used by the application programs 154, 254 the operating system 152, 252 the input/output device drivers 158, 258 and other software programs that may reside in the memory 136, 236.

With respect to FIG. 4, the data 156 may include participant or user profile type data 126 that defines a Publisher willingness to receive requests of publication of data from different Subscribers or topics for use by the circuits and modules of the application programs 154 according to some embodiments of the present invention as discussed further herein. For example, affiliated Subscriber hospitals or clinics may have a higher level of entitlement to receive records from each related or affiliated Publisher relative to non-affiliated entities. In other examples, non-affiliated but approved Subscribers (such as governmental agencies) may also have high-levels of entitlement.

With respect to FIG. 5, the data 256 may include electronic patient data records 226. The patient data records can comprise patient data records that have been mapped and parsed into patient data messages for use by the circuits and modules of the application programs 254 according to some embodiments of the present invention as discussed further herein. In some embodiments the patient data records held by a Publisher can include, for example, first name, last name, social security number, opaque identifier (used to provide patient-specific privacy while providing traceability to the source Publisher 200 and indirect traceability to the patient), gender, birth date, address, telephone number, birth place, blood type, age, height, weight, eye color, hair color, race and/or gene signature, such as a single nucleotide polymorphism (SNP), laboratory and/or tests and associated results, OTC (over the counter) or prescribed medications (current, past or prescribed for the current event), vaccinations, other past, current or prescribed therapies, diagnosis, discharge and admission dates, symptoms, demographic and geographic information (home, resident and/or work zip code, city, state, recent travel comments or observations), treating physician, workplace or other potentially toxic or hazardous exposures, and the like. As noted above, for some publication purposes, the patient personal identifier data can be removed from a message prior to its transmission to the Message Flow Server 100 (or in some other embodiments, by the Message Flow Server) to comply with local Publisher and/or regulatory rules. It will be understood that this list of patient data is provided for exemplary purposes only and that embodiments of the present are not limited to the attribute types set out herein.

As further illustrated in FIG. 4, according to some embodiments of the present invention the application programs 154 include one or more of: a User/Participant Registry Module 120, a Publisher/Subscriber communication protocol interface module 124, and/or a Subscriber accessible and selectable electronic topic catalog module 125. The application programs 120, 124, 125 may be located in a local server (or processor) and/or database or a remote server (or processor) and/or database, or combinations of local and remote databases and/or servers.

As further illustrated in FIG. 5, according to some embodiments of the present invention the application programs 254 include one or more of a message format standardization module 220 that can convert, map and/or parse patient data into a patient message format, a Publisher Message Flow Server interface module 224, and/or a publication rule or constraint module 234 which allows a respective Publisher to define their own publication rules for their patient data. The application programs 220, 224, 234 may be located in a local server (or processor) and/or database or a remote server (or processor) and/or database.

While the present invention is illustrated with reference to the application programs 120, 124, 125 and 220, 224, 234 in FIGS. 4 and 5, respectively, as will be appreciated by those of skill in the art, other configurations fall within the scope of the present invention. For example, rather than being application programs 154, 254 these circuits and modules may also be incorporated into the operating system 152, 252 or other such logical division of the data processing system. Furthermore, while the application programs 120, 124, 125 and 220, 224, 234 in FIGS. 4 and 5 are illustrated in a single data processing system, as will be appreciated by those of skill in the art, such functionality may be distributed across one or more data processing systems. Thus, the present invention should not be construed as limited to the configurations illustrated in FIGS. 4 and 5, but may be provided by other arrangements and/or divisions of functions between data processing systems. For example, although FIGS. 4 and 5 are illustrated as having various circuits and modules, one or more of these circuits or modules may be combined without departing from the scope of the present invention.

FIG. 6 illustrates an exemplary environment for operations and devices according to some embodiments of the present invention. As illustrated in FIG. 6, the Message Flow Server 100 can comprise a part of a hub environment 10h. Generally stated, the hub environment 10h is configured to provide content based routing for Publishers to Subscribers. As noted above, the hub environment 10h may also be configured to transfer messages from Publishers to only authorized Subscribers to route approved content-based messages to publication-specific approved Subscribers. The system can allow participants to identify content, format and/or destination for the types of clinical information the wish to receive (Subscriber view) and/or they are willing to provide (Publisher view).

As shown in FIG. 6, the hub environment 10h may include an Administrative Server 1100 that is in communication with the Message Flow Server 100. The hub environment 10h may optionally also include an AGPI (Anonymous Global Patient Identifier) server 1109. The AGPI may be configured as a J2EE device. As is known to those of skill in the art, the J2EE is a Java™ 2 Platform, Enterprise Edition (J2EE) standard for developing component-based multi-tier enterprise applications (Java is a trademark of Sun Microsystems in the United States, other countries or both). It will be understood that the message server 100 and/or Administrative Server 1109 illustrated in FIG. 6 may include all or a part of the data processing system or database environment discussed above with respect to FIG. 4. The web-based Administration Server 1100, that, in some embodiments, can also be called a web-based Administration Application, can also be configured as a J2EE device. The hub environment 10h can also include other features, such as products available through IBM's WebSphere® suite of products, such as a WebSphere Application Server, WebSphere MQ, a Tivoli® Directory Server (LDAP) or "Lightweight Directory Access Protocol", and a DB2® UDB (a "DB2 Universal Database", which is a Relational Database Management System (RDBMS) that leverages the On-Demand features of IBM's eServer™ iSeries™). WebSphere, Tivoli, DB2, eServer and iSeries are trademarks of International Business Machines Corporation in the United States, other countries, or both.

Figure 9:
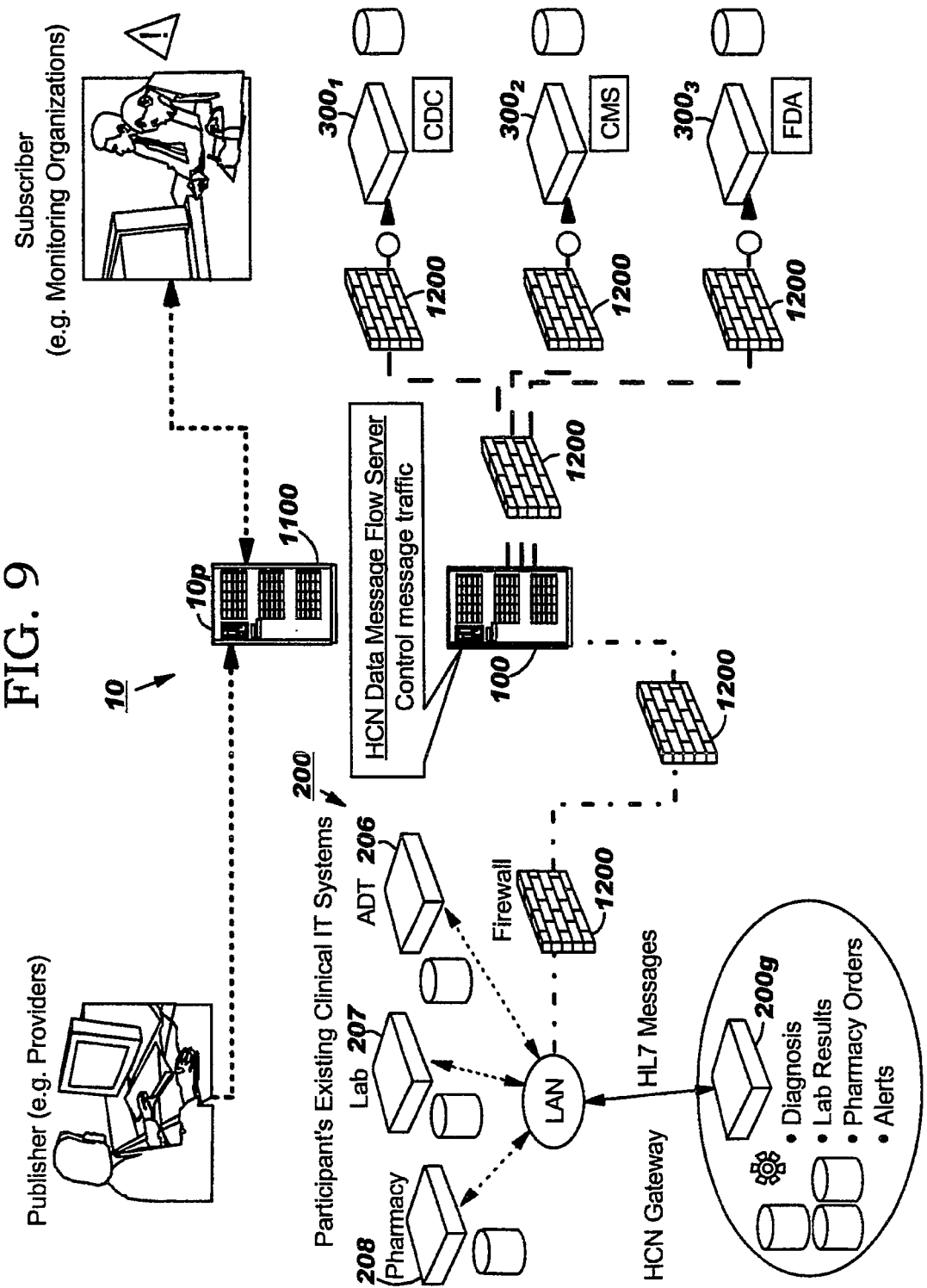
FIG. 9 is a schematic illustration of additional features of certain systems according to embodiments of the present invention.

FIG. 6 also illustrates that the hub environment 10h is in communication with a plurality of Publishers $200_1$, $200_2$, $200_n$ and Subscribers $300_1$, $300_2$, $300_n$. For a publication request for a particular selected topic from a Subscriber, $300_1$, the Administrative Server 1100 sends out notifications of requests for publication of the selected topic to one or more Publishers (shown as two Publishers, $200_1$, $200_2$) and receives responses back from those Publishers. The response can be a message approved for publication to the requesting Subscriber or a denial of the request. The response can also be a cancellation of a previous (or standing) publication approval for a particular topic. The Message Flow Server 100 then sends all approved publication messages from respective Publishers to the requesting Subscriber $300_1$. The Administrative Server 1100 can pre-screen participants and levels of authorization or participation to send Subscriber requests only to potentially willing Publishers and the like. The messages to and from Publishers and Subscribers can be transmitted via the Internet using SSL (Secure Sockets Layer) channels, encryption and/or other secure data transmission means. The network system can include at least one domain firewall 1200. Typically, more than one firewall is used including hospital hub and Subscriber firewalls 1200 (FIG. 9).

As will be discussed further below, referring to FIG. 6, the Publisher Gateways $200g_1$, $200g_2$, $200g_n$ can be configured to connect to a respective Publisher participant's institutional computer systems and/or information technology systems (represented by reference number 500 in FIG. 11A) to receive, aggregate and/or accept electronic data records that can be correlated to particular patients or other desired criteria.

The Subscriber Gateways 300 can include or be in communication with a repository database in which they can store the publications of messages received in response to topical data requests (or for certain Subscribers or observers, a repository of messages and/or alerts).

In particular embodiments, the gateways 200, 300 can employ JAVA and/or IBM WBI code or other suitable program code. The Publisher Gateways 200 can include an XML-based patient "de-identification routine" that removes the personal identifiers (name, social security number and the like) from patient data messages. The Publisher Gateways 200g can also include: a document transform routine whereby patient data records are transformed from HL7 messages to CDA XML documents, HL7 parsing (a messaging HL7 toolkit which may be carried out using Chameleon from iNnterfaceware, located in Toronto, Canada), and Websphere Business Integration products, DB2 UDB, and HL7 TCP/IP sockets to WBI Connectors.

FIG. 7 illustrates that the Publisher and Subscriber Gateway 200g, 300g can be provided as a common gateway 200gc that implements both functions. FIG. 7 also illustrates that the AGPI (Global Patient Registry or Identifier) server 1109 can communicate directly with Publisher Gateways 200g to provide a common patient registry service to the respective Publisher Gateways 200g.

Figure 8:
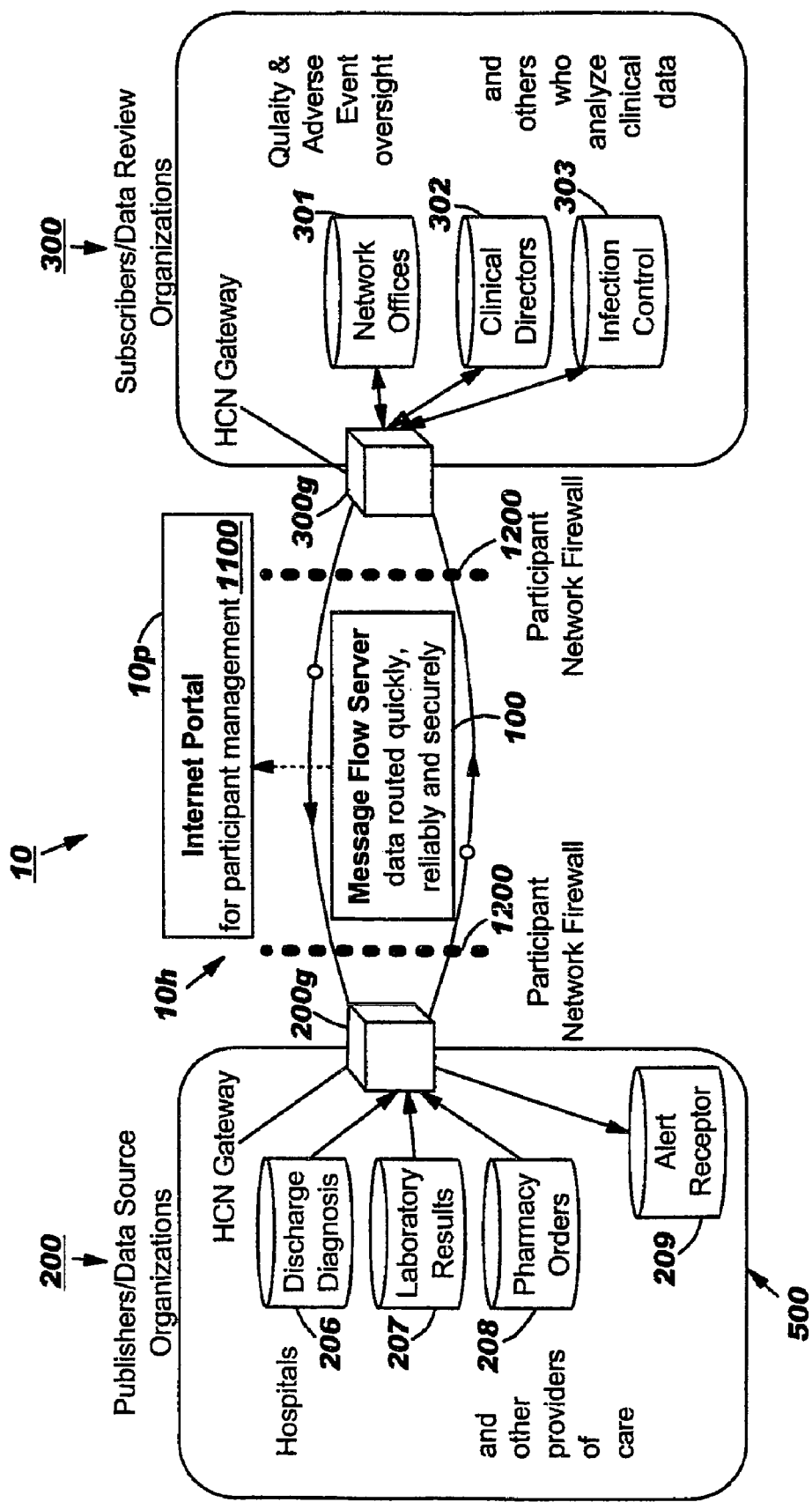
FIG. 8 is a schematic illustration of exemplary system architecture for a networked system according to embodiments of the present invention.

FIG. 8 illustrates an exemplary architecture for a collaborative data network system 10. The system 10 includes an Internet portal or hub 10h with the Message Flow Server 100 and participant network firewalls 1200. As shown, each Publisher site 200s can include at least one Publisher Gateway 200g that communicates with various linked (internal and/or external) service providers or data collection stations, such as, but not limited to, a hospital billing and/or administration system 206 (which can provide a discharge or intake diagnosis), laboratory 207 (that can provide laboratory or test results or tests/evaluations ordered), a pharmacy 208 (for input of drug orders), and other relevant data collection inputs. The Publisher Gateways 200g can be configured to filter, link and map healthcare data elements based on Publisher-specific business rules or constraints that they select, approve and/or define.

One example of a local business rule can be that patient records are checked to see if all recommended tests or procedures have been completed based on a diagnosis. Also the system can monitor and identify patients diagnosed with a certain disease or impairment and correlate the follow-up lab results to confirm the diagnosis. These checks or rules can drive patient care improvements, facilitate proper treatment and/or help manage disease outbreaks. In some embodiments, the results or data summaries of the patient records can be shared within an organization rapidly and reliably using WebSphere MQ from IBM. The system 10 can be used to track outcomes in a rapid and error-reduced or error-free manner that is better than conventional chart-pulls that are delayed or prone to more errors. This type of automated reporting can facilitate compliance with audit plans or requirements.

The gateway 200g can be in communication with an alert receptor 209 whereby data gathered and/or provided by the gateway 200g can be electronically monitored to generate an alert to internal and/or external authorities and/or administrators when certain abnormal conditions are identified. The alert receptor 209 can be a separate module and/or database at a Publisher 200 that communicates with the gateway 200g or can be integrated into the gateway 200g. For example, the alert receptor 209 can detect a rise in the number of patients admitted for a certain condition and/or identify possible widespread health concerns, such as a food poisoning diagnosis, identification of an anthrax exposure or spinal meningitis in one or more patients, a bioterrorism exposure, an increase in prescriptions for a certain drug or drug type (such as those identified as addictive or with higher mortality risk), adverse drug events and the like.

FIG. 8 also illustrates that a Subscriber (organization or site) 300 can include one or more affiliated entities (that may be local or remote with respect to each other) that can provide quality and/or adverse event oversight or analyze clinical data and connect to a Subscriber Gateway 300g. As shown, a Subscriber 300 can include a network office(s) 301 and clinical director(s) 302, and infection control official, organization/entity 303. The Subscribers can create a topic (define the parameters of the data requested) and subscribe and/or select a topic (define a respective Subscriber's specific interest in a topic).

As noted above, the Subscriber site and the Publisher 200 can be a common Publisher and Subscriber site that employs a common gateway 200c (FIG. 7) that can act in either a Publisher or Subscriber mode. The alert receptor 209 and Publisher Gateway 200g and/or the Subscriber 300 can be used to monitor patient care processes and quality of care and can be used to generate reports such as that shown in FIG. 12. Alternatively, or in combination with the report features that may be provided by the system 10, the Subscribers 300 can be configured to generate their own reports using data received from the system, which may be stored in respective Subscriber databases.

FIG. 9 is a schematic illustration of different components in an exemplary collaborative healthcare data sharing system 10. As noted above, the system 10 can include a web portal 10p that controls participant access and communicates with the Message Flow Server 100 that controls message traffic. The web portal 10p may be a single federated or even global portal or a linked system of several portals, such as separate portals for foreign or selected networks, and the like. The system 10 allows participants to define data sharing rules, select what data to share and decide with whom to share, and monitor, alert, notify, and report on selected topics and provide account activity.

Figure 10:
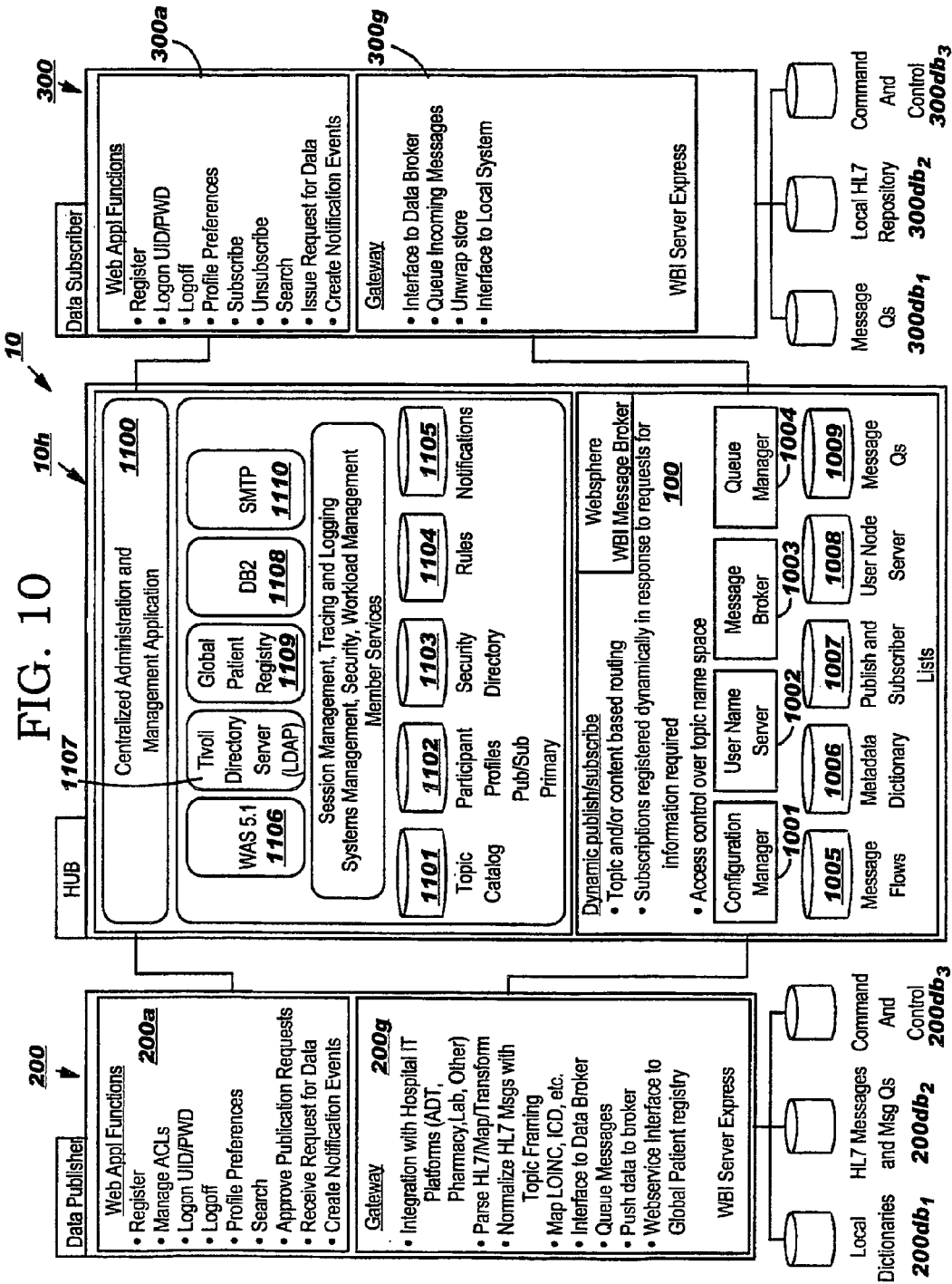
FIG. 10 is a schematic illustration of a system that includes a hub that interfaces with Publishers and Subscribers according to embodiments of the present invention.

FIG. 10 illustrates a more detailed architecture of an exemplary web based data sharing system 10 according to some embodiments of the present invention. As shown, the hub 10h comprises a server 1100 that provides a centralized administration and management application. The Administrative Server 1100 can be configured to provide session management, tracing and logging systems management, workload management and member services. The Administrative Server 1100 can include or communicate with a plurality of databases including: a topic catalog 1101, participant (Subscriber and Publisher) profiles 1102, a security directory 1103, publishing or routing security rules 1104 and notifications 1105. The Administrative Server 1100 can include several sub-servers for integration into web systems, such as, but not limited to, a WAS (web application server) which may comprise an IBM WebSphere Application Server, a Tivoli Directory Server (LDAP), a AGPI (Global Patient Registry or Identifier) Server 1109, a DB2 Server, and a SMTP (Simple Mail Transfer Protocol) Server 1110. It is noted that although described herein as "servers" other suitable computer configurations may be used.

The topic catalog database 1101 (FIG. 10) can be an electronic catalog or listing of Subscriber selectable topics (which may include a topic name and a topic description) such as those shown in FIG. 15. The topic catalog can be presented in alphabetical order (such as when a complete listing is provided) or may be searchable using a key work input as also shown in FIG. 15. If a Subscriber wants to request data for a topic that is not in the catalog, the Subscriber can enter the request as a "new" topic entry that can be saved and reviewed to see if it meets publication rules. Once in the catalog, a Subscriber can request data on that topic, but the hub 10h (either the Administrative Server 1100 or the Message Flow Server 100) can select which (if any) Publishers to send the request to publish healthcare data on the new (or existing) topic based on previously established Subscriber and/or Publisher participation rules and the like. The notifications database 1105 can be used to provide a notification summary such as shown in FIGS. 14 and 16A. As shown in these figures, a Publisher can view notification details including date, time, type, from, and subject. The Publisher can also review publication requests, which provide a requesting Subscriber's identity/name and the requested topic. The screen views shown in FIGS. 14 and 16A can be configured as a Publisher "home" screen view.

Referring again to FIG. 10, the Message Flow Server 100 can be configured to dynamically publish and/or subscribe selected topics of interest from participating Publishers to participating (approved) Subscribers and implements the publish/subscribe communication protocol. The Message Flow Server 100 can comprise a message broker such as a WebSphere WBI (WebSphere Business Integration) message broker that can provide topic and/or content based routing, register subscriptions dynamically in response to requests for selected information, and provide access control over a topic name space. The Message Flow Server 100 can include one or more sub-servers, clients or managers, such as, but not limited to, a configuration manager 1001, a user name server 1002, a message broker 1003, and a queue manager 1004. The Message Flow Server 100 can comprise and/or communicate with several databases or servers, clients and the like, such as, but not limited to, a message flow database 1005, a metadata dictionary 1006, publish and Subscriber lists 1007, user node server 1008, and a message queue database 1009.

As also shown in FIG. 10, the Administrative Server 1100 can be configured with web application functions that appear at Publisher portal sites 200s. The server 1100 may comprise and/or be configured as a WBI servers express. The web application can be used to: allow a user to register as a participant, manage ACLs (Access Control Lists), logon UID/PWD (using universal ID or password access), logoff, define profile preferences, search, approve publication requests, receive request(s) for data, and create notification events.

The Publisher Gateway 200g can be configured to integrate with hospital or other Publisher IT (information technology) environments or platforms 500 such as pharmacy, lab, ADT (Admission, Discharge and Transfer) and the like. The gateway 200g can also be configured to do one or more of: parse HL7 data, map and/or transform incoming data, normalize incoming data into HL7 messages with topic framing, map LOINC, ICD codes, interface with the Message Flow Server 100 at the web portal, queue messages, push data to the data broker, and/or provide a webservice interface to the Global Patient Registry 1109 at the hub 10h. The gateway 200g can be in communication with and/or comprise a plurality of databases, such as, for example, a local dictionary or dictionaries $200db_1$, HL7 messages and message queues $200db_2$ and a command and control database $200db_3$.

Table 1 illustrates exemplary HL7 supported events with a topic description and associated code.

TABLE 1

| Currently Supported HL7 Events | |
|---|---|
| ADT A01 | Admit a patient |
| ADT A02 | Transfer a patient |
| ADT A03 | Discharge a patient |
| ADT A04 | Register a patient |
| ADT A08 | Update a patient |
| ADT A09 | Patient Departing |
| ADT A11 | Cancel Admit |
| ADT A13 | Cancel Discharge |
| DFT P03 | Detailed Financial Transaction |
| OMP O09 | Pharmacy/Treatment |
| ORM O01 | General order |
| ORU R01 | Observation Result |
| RDE O11 | Pharmacy/Treatment encoded order |
| RDS O13 | Pharmacy/Treatment dispense |
| VXU V04 | Vaccination Record update |

Additional HL7 messages can be implemented as part of a configuration as desired.

FIG. 10 also illustrates a Subscriber portal site 300s that communicates with web application functions 300a. As for the Publisher site, all or some of the web application functions can be carried out by the Administrative Server 1100. The web application functions can be used to: allow a Subscriber to register as a participant, logon UID/PWD, logoff, define profile preferences, subscribe, unsubscribe, search, issue request for data, and create notification events. The gateway 300g can be configured to interface with the Message Flow Server 100 at the web portal, queue incoming messages, unwrap store and interface to a local IT system. As shown, in FIG. 10, the gateway 300g can include or communicate with a plurality of databases including a message queue database 300$db_1$, a local HL7 repository of received messages 300$db_2$, and a command and control database 300$db_3$.

Figure 11A:
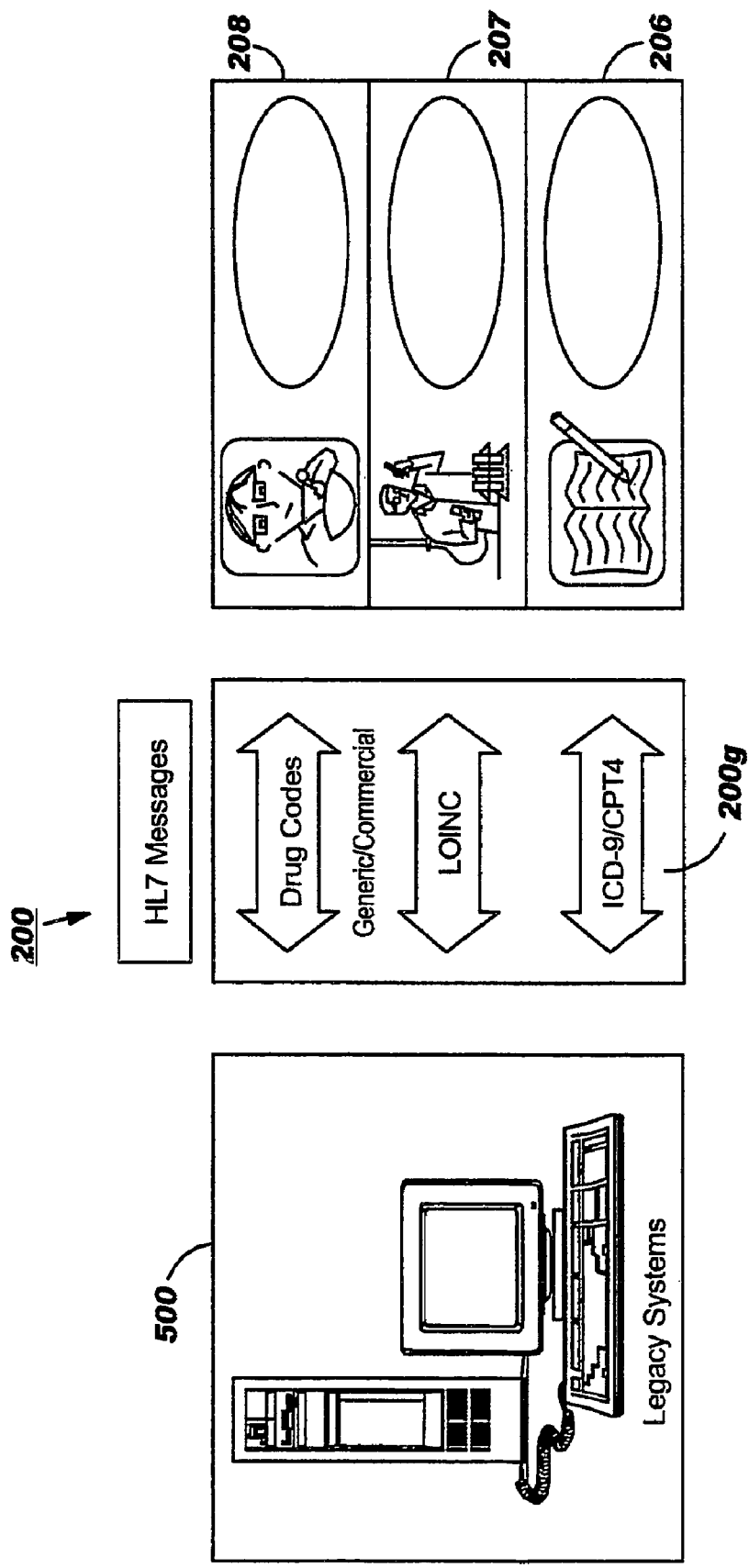
FIG. 11A is a schematic illustration of a system of accumulating patient record data according to embodiments of the present invention.

FIG. 11A illustrates that each or some of the Publisher sites 200s can have their own (and typically different) legacy or existing IT system 500 with one or more networks of data input sources 206, 207, 208 that may employ different codes or classification systems within that environment. Thus, Publisher to Publisher, the data sources can be different. In addition, the systems used to collect and report patient data can be different Publisher to Publisher. However, embodiments of the present invention provide for Publisher-specific "on-boarding" so that the Publisher Gateway 200g is customized to collect, interpret data from local systems and configure that data into standardized formats as appropriate so that external communications of published data from respective Publishers 200 is standardized within the collaborative data sharing system 10.

For example, at a respective Publisher site 200s the pharmacy 208 can use drug codes (generic/commercial), the lab 207 can use LOINC codes and the administrative input records 206 (admission, discharge, diagnosis and transfer or other patient care records) can use CPT4 codes. These disparate codes/classifications can be converted into a standard message format, typically using HL7 messages. Input from each source can be correlated to a particular patient record and stored in a message database as described above. As noted above, the Publishers 200 can send a topic publication message in a format that can include a content definition header, which can be in a different format from other data elements in the topic publication message (such as in XML). Typically, the data to be transmitted with the header is enclosed in the body of the message (called an envelope or enclosure), and what resides in the envelope can generally be data in any arbitrary industry specific format.

Figure 11B:
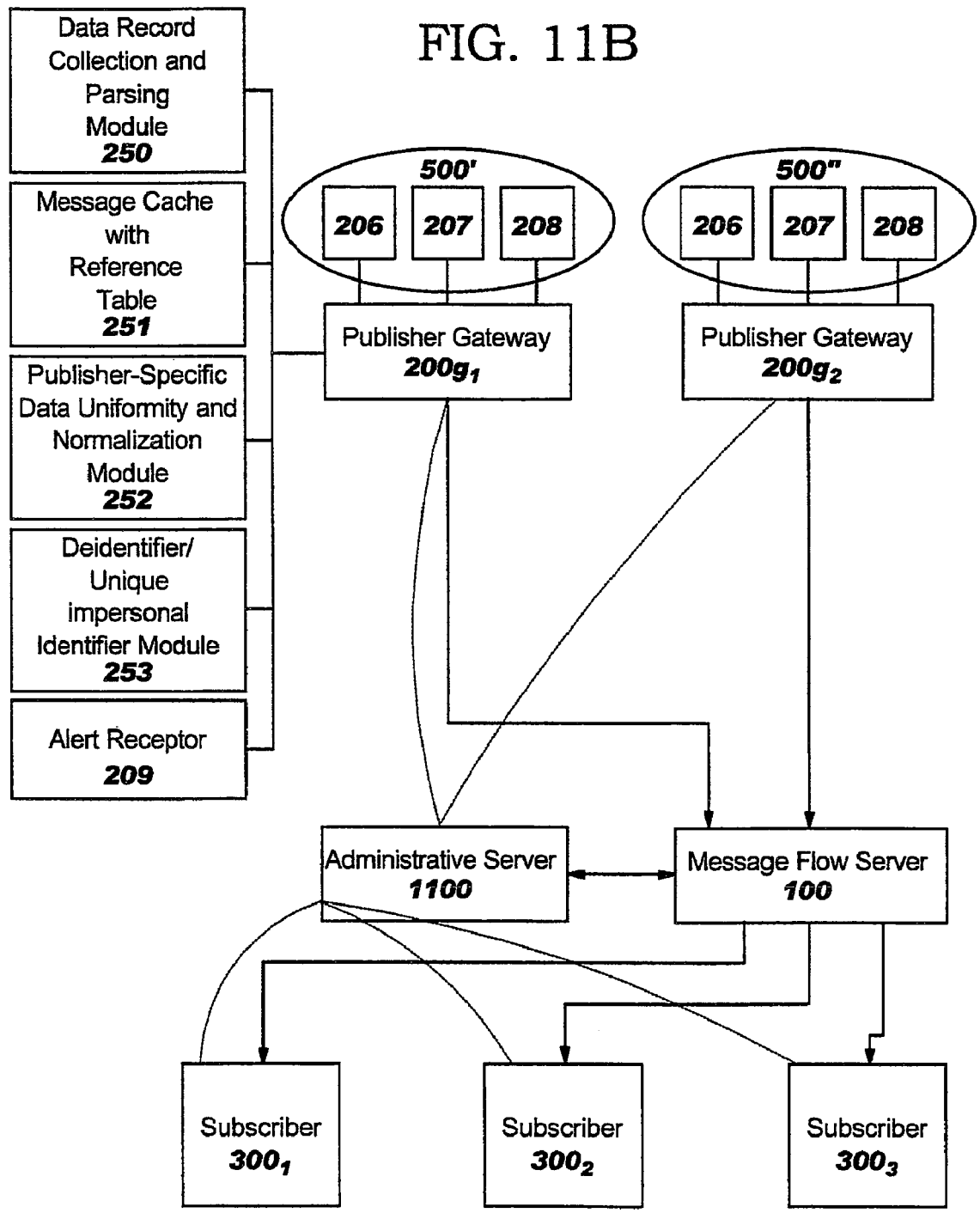
FIG. 11B is a block diagram of a collaborative data sharing system with Publisher Gateways configured to support local IT (Information Technology) specific data systems according to embodiments of the present invention.

Referring to FIGS. 10 and 11B, the Publisher Gateways 200g may be configured to: (a) cache patient data for a desired time interval to allow for relevant data to be aggregated and/or compiled into a patient data record prior to publication or posting of a patient data message and/or prior to mapping the patient data to a patient data record message in standard message format; (b) de-identify or remove certain patient information from a patient record prior to publication (to provide anonymous and/or HIPAA privacy compliant data); (c) map and/or normalize incoming data into standardized messages, event descriptors and/or commonly accepted medical reference codes (such as Logical Observation Identifiers Names and Codes classifications "LOINC", International Classification of Diseases classification codes ICD-9, ICD-10, and the like) to convert local data to standardized formats; (d) perform message parsing such as parsing HL7 and XML data types; and (e) apply local business and/or data-use/publication rules.

In some embodiments, the Publisher Gateways 200g are configured to automatically electronically correlate incoming data, correct electronic patient data records that have improperly formed HL7 messages, convert non-standard HL7 observation messages in electronic patient data records to standard HL7 messages, convert drug orders from a non standard HL7 observation to a standard pharmacy order message, map local Publisher codes for Admission Source and Discharge Disposition to HL7 recommended codes and/or data fields, and map local codes for laboratory observations to a generally accepted industry standard system of laboratory tests/results (LOINC).

FIG. 11C illustrates exemplary operations that can be carried out by respective Publishers to collect and correlate patient event data records according to embodiments of the present invention. FIG. 11D illustrates exemplary operations that can also be carried out by respective Publishers to search for requested data using in situ defined search criteria that electronically automatically identifies relevant data elements based on a requested publication request/topic and extract and publish data according to embodiments of the present invention.

Referring to FIG. 11C, in some embodiments, a respective Publisher Gateway can electronically collect data from multiple data sources for a respective patient event (block 260). The collected data can be correlated, parsed into data field segments and compiled into an electronic patient event data record having parsed searchable field segments of data (block 262). The patient event data may be cached for an interval so that associated patient and/or event data can be collected and correlated together (block 263). That is, as data flows into the Publisher Gateway, the data can be first cached (in an electronic "holding area" for a period of time so that associated data for that patient and/or event can be compiled into a more complete data message for that event/patient). The cache can employ a reference table that can be used to look back in time to determine what messages have already arrived. The compiled electronic data records can be stored in an electronically searchable record database (block 264). The "complete" data for a patient event record may be stored in the cache database or a separate record storage database. The patient event data records can be configured as patient data message records having parsed searchable message subfields of patient event data (block 265).

The data records can be normalized by changing certain local formats of data into defined uniform system-wide formats (block 266). The compiled patient event data records may optionally be stored for a relatively short duration of less than about six months, and typically less than about three months (block 267). The messages 200m (see, e.g., FIG. 13) can be normalized (standardized) as they are received, before they are stored in the message database, or anytime prior to an outbound publication. The normalization is configured to transform local codes or local nomenclature into system wide codes, nomenclature and/or formats. That is, the Publisher Gateway can review all fields in a patient data record message, identify non-standard nomenclature or codes and transform the local non-standard nomenclature into an accepted system-wide uniform nomenclature of format. In operation, the Publisher Gateway 200g can receive data, inspect data, identify irregularities in the incoming data and create a new grammar to account for the irregularities. In some embodiments, an operator can approve the changes before they are entered into the system or Gateway database. In other embodiments, the Publisher Gateways 200g can automatically electronically map the incoming data (in script) according to manually defined input or correlation scripts identified during the "on-boarding" process. For example, if a local system uses a character "M" to denote discharge disposition to a Rehabilitation Department or Facility, instead of "R" which is the standard for the system, the Gateway can transform the "M" into an "R". Similarly, the Gateway can map local codes to standardized system codes. For example, in clinical laboratory systems, if the lab generates "Panel G", the Publisher can map the appropriate LOINC code that replaces the non-standard "Panel G" code or term.

Referring to FIG. 11D, a request from a Subscriber for specified data is received (block 280) by the Publisher Gateway. A respective Publisher approves (block 282Y) or denies (block 282N) the request (typically once). As noted above, once approved, a "subscription" may be authorized using the Administrative Server 1100 and/or Message Flow Server 100 so that future data records matching the topic can be forwarded automatically (until the subscription is canceled by the Publisher or expires).

If approved, the Publisher Gateway can review the requested data and establish associated data request rule criteria to be applied to filter and search for the event data requested by the Subscriber in that Publisher's data records (block 284). For example, a Subscriber data request may specify a particular diagnosis, age and/or gender. As such, a rule criteria for this request can be: "Diagnosis=Anthrax, Sex=M, and Age gt 65" (where "gt" is greater than). The rule criteria can also define what data elements will be included in an automatic publication to the Message Flow Server when, and if, a Publisher patient data event record is determined to match a Subscriber data request. The rule criteria for each approved request can be stored for future use to be applied to filter new records that are received (typically as they are received) at the Publisher Gateway (block 285). The stored data records can be automatically electronically examined to identify relevant data records (block 286).

During the electronic examination or searching of the stored data records, the Publisher Gateway can examine and parse each stored patient record (typically a patient message record) looking for relevant and matching values and/or data elements to determine if there are any of their records that match the requested and approved data request. As noted with respect to FIG. 11C, the Publisher Gateway may cache certain incomplete and/or altered patient data records for a desired interval to compile or correlate other event-related data associated with that record that may occur (block 287). The Publisher Gateway publishes relevant patient data to the Message Flow Server (block 288). The Publisher Gateway can automatically electronically search or interrogate all new incoming data records or changed data records to identify potential matches to approved data requests using the defined Rule Criteria (block 290).

As noted above, based on a defined privacy level associated with the Publisher and/or requesting Subscriber, certain subfields in the message record can be suppressed or de-identify personal information. In some embodiments, a unique system identifier can be added to a message publication.

Table 2 illustrates data elements that can be monitored and/or tracked using messages according to some embodiments of the present invention.

| DATA ELEMENT | DISEASE STATE |
|---|---|
| General | |
| Admitting Diagnosis | All |
| Discharge Diagnosis | All |
| Discharge Disposition | All |
| Gender | All |
| Admission Source | All |
| Race | All |
| Diagnoses | |
| Anthrax Diagnosis | Anthrax |
| Legionella Diagnosis | Legionella |
| AMI Diagnosis | AMI |
| Diabetes Diagnosis | Diabetes |
| Stroke Diagnosis | Stroke |
| Pneumonia Diagnosis | Pneumonia |
| Observations | |
| Respiratory Viral Results | Respiratory |
| Varicella Test Results | Varicella |
| HDL Cholesterol | Diabetes |
| LDL Cholesterol | AMI, Diabetes |
| Triglycerides Result | Diabetes |
| Positive Pregnancy | Adverse Drug |
| Medications | |
| ACE Inhibitors | AMI |
| Antibiotic | Pneumonia |
| Felbatol | Epilepsy |
| Thalidomide | Leprosy |
| Antithrombotic | Stroke |
| Nifedipine | Stroke |

The examples are for illustration only and are not to be limiting to the scope of the invention, as the types of topic data categories and elements are not limited to those shown in the examples.

FIG. 11B illustrates that a plurality of support modules 250, 251, 252, 253 and 209, some of all of which may reside within the Publisher Gateway 200g or may reside in supporting databases and/or devices in communication therewith, can be used to carry out one or more of the Publisher functions described herein. The Publisher Gateway 200g can be described as having "incoming" data collection duties and "outgoing" duties whereby approved and authorized Subscriber 300 requests for data are considered, and internal records are compared, filtered and matched to the data requests and published (as appropriate) to the Message Flow Server 100. The Administrative Server 1100 communicates with each participant via the web portal and with the Message Flow Server 100 as discussed above to control the communications to authorized users. As also shown in FIG. 11B, the different data sources 206, 207 and 208 may communicate directly with the Publisher Gateway 200g. In other embodiments, may indirectly communicate with the respective Publisher Gateway 200g such as via a clinical data source collector. Combinations of the direct and indirect communication protocol and systems may also be employed.

FIG. 11B illustrates two Publishers 200, each having respective local IT systems 500', 500", respectively. The local systems 500', 500" each comprise data sources 206, 207, 208. Each Publisher Gateway $200g_1$, $200g_2$ is configured to collect the data and manipulate the data into standardized forms for potential sharing with authorized Subscribers 300. Although the support modules 250-253 and 209 are shown only for the first Gateway $200g_1$, the same or similar modules can be used for other Publishers 200.

Figure 12:
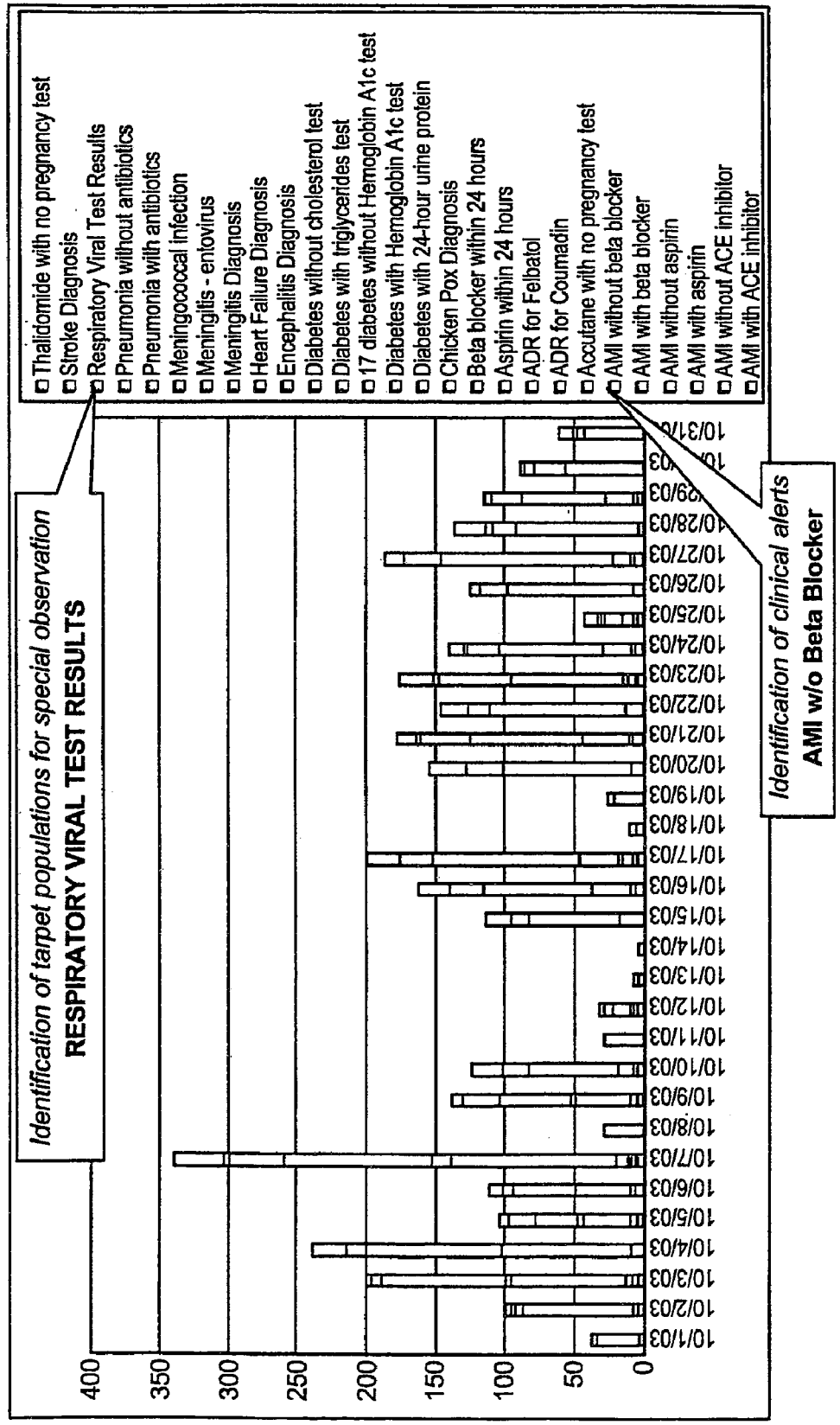
FIG. 12 is a graph of a data summary of topical events that can be generated according to embodiments of the present invention.

FIG. 12 illustrates that a data flow summary of different events that can be compiled for oversight or business needs or desires of a particular participant. As shown, a chart of aggregate messages by date and type of event/healthcare issue can be provided. Such information can be used to identify target populations that may be flagged for special observation (such as respiratory viral test results), or generate clinical alerts (such as when a patient with Acute Myocardial Infarction has not been identified as ordered a beta blocker medication within a certain time frame from admission). The reports can be customized and/or automatically generated according to different local uses. FIG. 15 illustrates a sample view of an activity summary at a Publisher Gateway 200g using the portal 10p to view internal, Publisher-specific messages by topic name. Alternatively, or in combination, in some embodiments Subscribers 300 can be configured to generate desired reports using their requested/received publication data. Table 3 illustrates some examples of "key" data elements that can be tracked by a participating agency, particularly a governmental agency, to evaluate quality of care and/or trends in health.

TABLE 3

| KEY DATA ELEMENT | ADDITIONAL |
| --- | --- |
| Observations | |
| AMI Diagnosis (GE 65) | All Labs and Med Info |
| AMI Diagnosis LT 65 | All Labs and Med Info |
| HF Diagnosis GE 65 | All Labs and Med Info |
| HF Diagnosis LT 65 | All Labs and Med Info |
| Pneumonia Diagnosis GE 65 | All Labs and Med Info |
| Pneumonia Diagnosis LT 65 | All Labs and Med Info |
| Meningitis | All Labs and Med Info |
| Medications | |
| Coumadin | Pro thrombin time |

FIG. 13 is an example of a message 200m that includes three data message segments, lab data 200l, pharmacy data 200p and diagnosis data 200D for a patient. The message 200m was approved and submitted for publication to the Message Flow Server 100 for transmission to the requesting Subscriber(s). The message identifies the topic "Stroke Diagnosis" and includes an associated rule name of "Stroke Diagnosis", a Provider identifier and a Global patient identifier number (Patient ID) with a message time stamp.

Figure 16B:
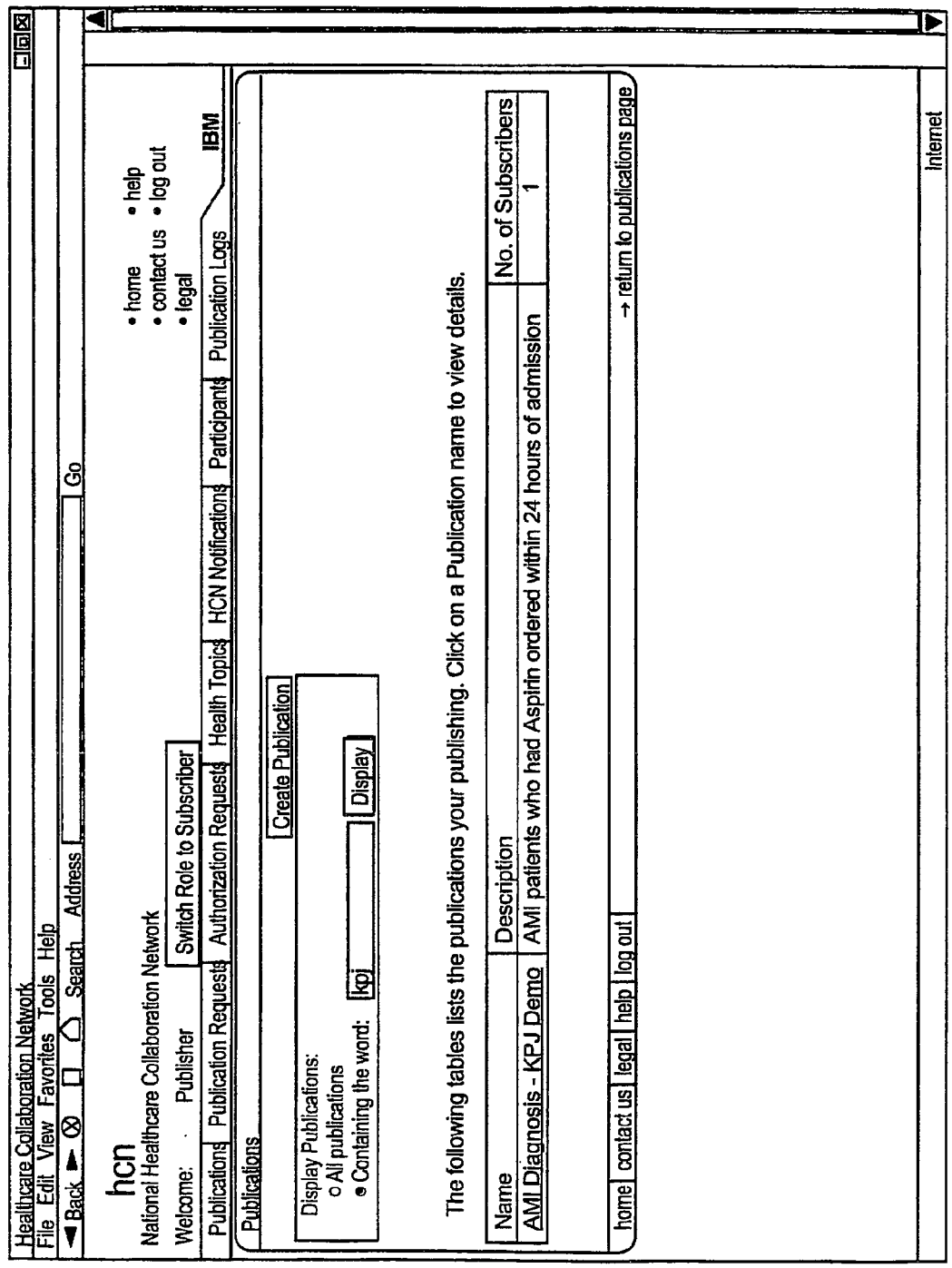

FIG. 16A illustrates the Publisher viewing and use mode and FIG. 16B illustrates that under a publication mode, a Publisher can view publications that are publishing with the details of same (and a Publisher can cancel the publication if desired). The Publisher can create a publication (agree to provide data for a topic subscription), view publications (list the details of publications—all or select records), and delete a publication (allows the Publisher to delete an existing publication). The participant Publishers can generally stream all supported data to their gateway 200g on a continual basis for all patients. The clinical systems can generally stream (send) the data in the form of HL7 messages. Their respective gateways 200 can store their patient messages for a desired time as noted above.

Figure 17A:
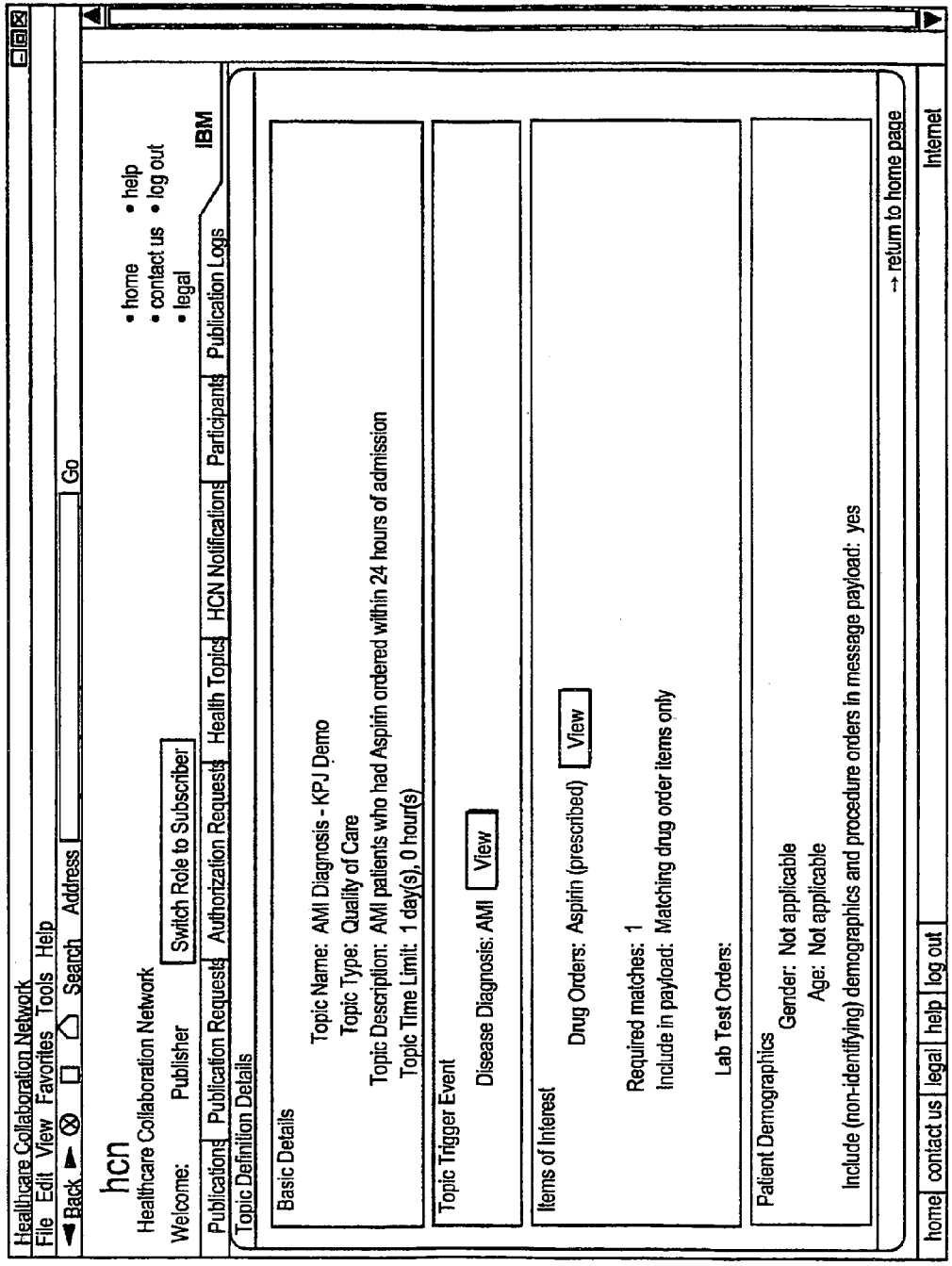
FIGS. 17A-17C are screen views that can be used to view publication details of a topic(s) of interest according to embodiments of the present invention.

FIG. 17A illustrates that a user can electronically select to go to a Subscriber mode. FIG. 17A illustrates some details of a selected topic ("topic definition details") that a Subscriber can identify or select to obtain healthcare records of interest (if the Subscriber is authorized for same according to defined rules). The topic includes a topic trigger event (shown as a disease diagnosis of "AMI" or acute myocardial infarction), items of interest (shown as a drug order of aspirin) so that only records that indicate matching drug order will be included in the returned data, and whether demographic data is of interest or whether the request is further limited by same. Once a topic is created and stored in the topic catalog, it can be used by all Subscribers as long as their respective use entitlement (privacy provisions or entitlements) are compatible with the topic.

The system 10 provides filters that allow a participant to limit the content of data sent. By default, typically, all filters are applied and the Subscriber will receive data for all types of data supported by the system. The participant can "turn off" or deselect one or more filters. In such case, the system 10 can send data matching the topic events and data for categories that were not filtered.

The primary purpose of a "topic event" function is to select patient records with relevant data. The topic event function can also impact the content of the data. For example, a first occurrence of any topic events marks the begin bracket for messages to be sent and the first occurrence of the last topic event marks the end bracket of messages that will be sent. The order in which topic events are matched is generally not considered. All messages which occur between the start and end bracket will be sent if other rules do not override this procedure. If a topic event is a diagnosis, the begin bracket can be admission and the end bracket discharge (typically the entire patient encounter). The Subscriber can limit duration by specifying a time duration. If duration is identified, then the evaluation begins with admission and ends with the time limit is reached. If all topic events and specified demographic data are not matched during the time specified, no data message record will be sent. Data can be sent when all topic events are matched. Typically, however, a participant cannot specify when data is to be sent.

Once a trigger event is received at a Publisher from a Subscriber (via the Message Flow Server 100), the Publisher evaluates stored messages and subsequent messages for a patient to see if the patient(s) exhibit all specified criteria.

Figure 17B:
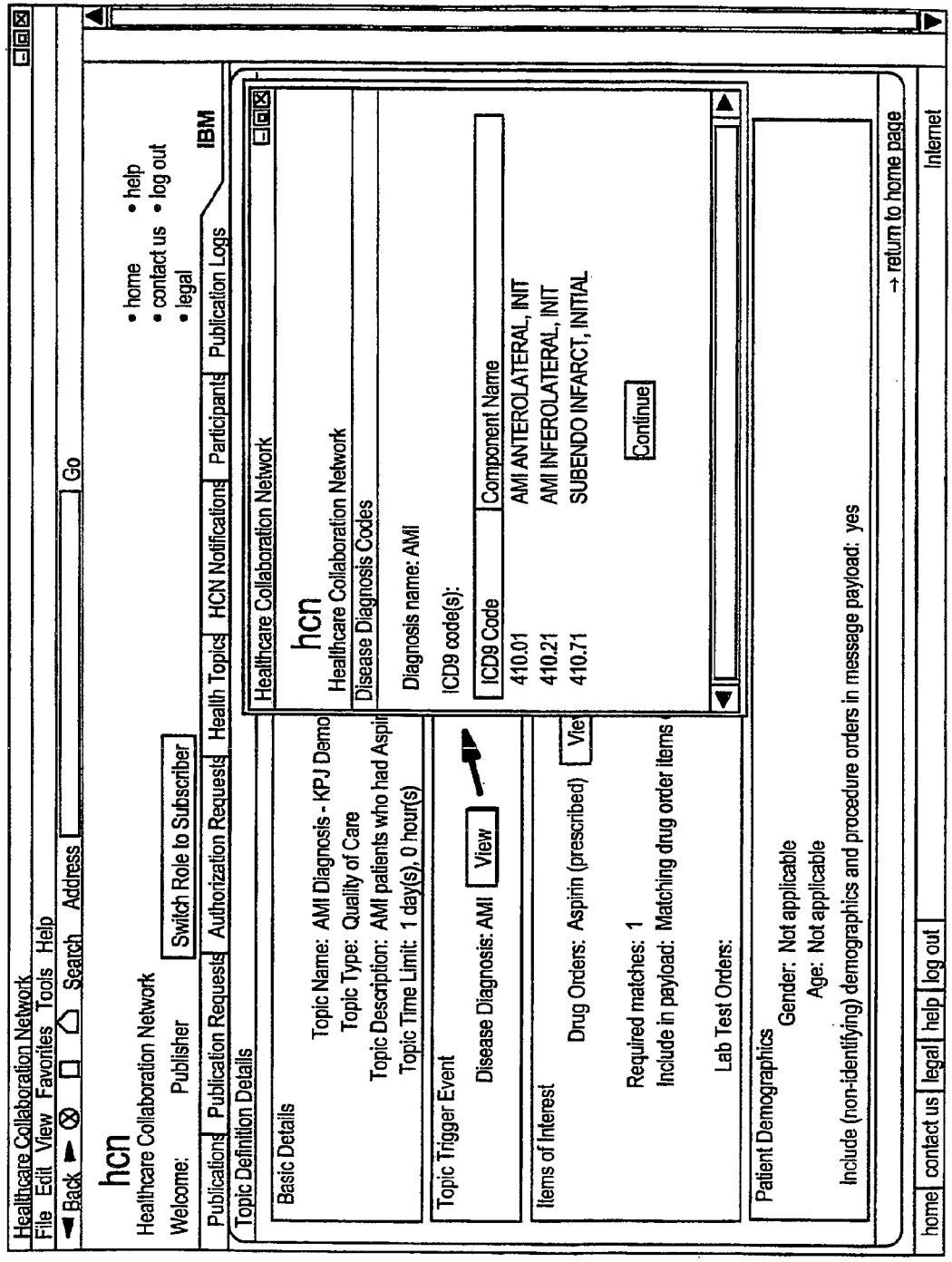
Figure 17C:
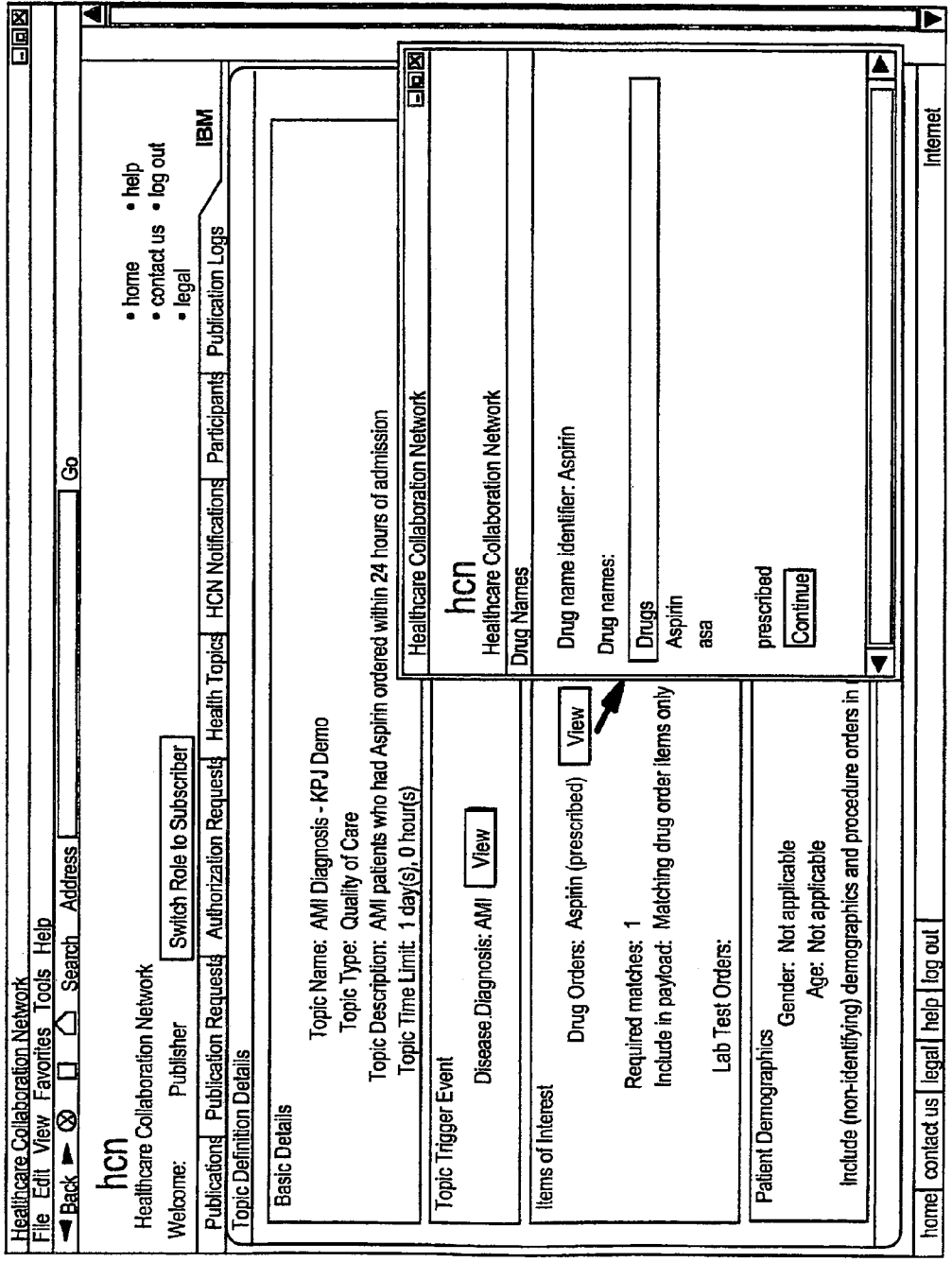

FIG. 17B is a screen view of further information regarding the trigger event field that can be accessed via the "view" button. As shown, for the diagnosis name "AMI" is associated with three ICD-9 codes, 410.01, 410.21 and 410.71. Records matching one or more of these codes can be included based on this requested trigger event. For a diagnosis, the participant should define all related variations and valid ICD-9 codes. Similarly, FIG. 17C illustrates further information regarding the aspirin drug order can be obtained via the associated view button. As shown, for a drug name identifier of "aspirin", records that have drugs prescribed under "aspirin" or "asa" will be included.

Typically, the system 10 can receive lab and procedure observation/result messages that contain the order ID and associated LOINC, CPT or ICD-9 code from the order. If participants (Subscribers) want data regarding lab or procedure orders, a lab or procedure result should be specified as a topic event category for additional data. If an event is defined by a lab result, the participant should specify all desired variations of the lab test using corresponding LOINC codes. The participant can also specify results criteria under topic events. If the event is a procedure, the participant should specify all desired variations of the procedure that are valid values for each procedure specified and should have a corresponding valid ICD-9 or CPT code. The participant can specify if ICD-9 and/or CPT codes should be used.

Embodiments of the invention can be used to automate quality and compliance reporting as well as clinical data sharing with federal and state agencies like the CDC (the Centers for Disease Control), the FDA (Food and Drug Administration), the NIH (the National Institutes of Health) and the CMS (the Centers for Medicare and Medicaid). Other federal agencies that may potentially participate in collaborative data sharing systems include the DOD (Department of Defense), the FAA (the Federal Aviation Agency, the FBI (Federal Bureau of Investigation), the Department of Homeland Security and the like. In some embodiments, the systems of the present invention can harness existing electronic data available in many provider settings, such as ICD, CPT, LOINC, and NDC via HL7.

Figure 18:
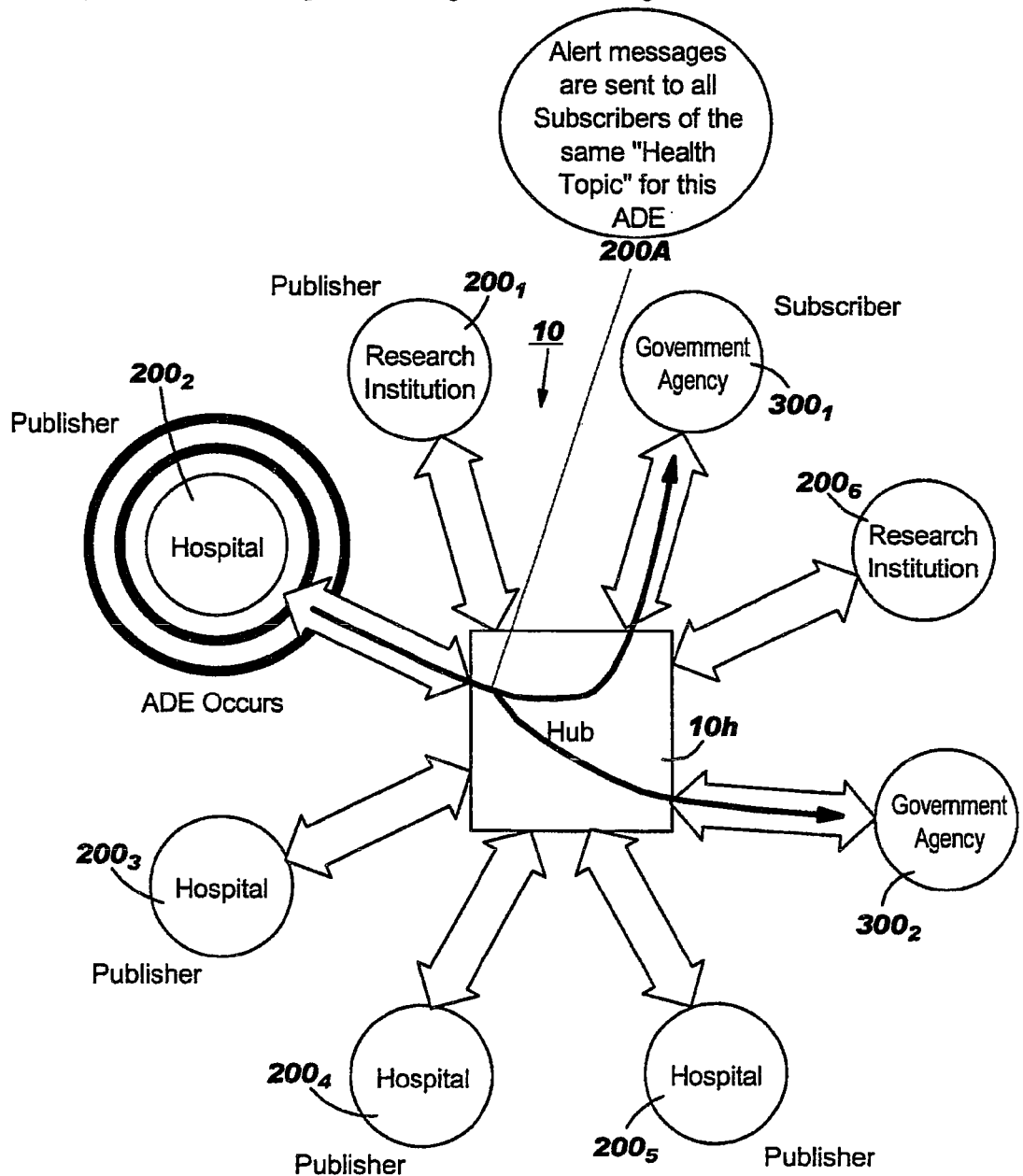
FIG. 18 is a schematic illustration of a healthcare system used to identify and generate an Adverse Drug Event alert according to embodiments of the present invention.

FIG. 18 illustrates that embodiments of the present invention can be used to identify adverse drug events (ADE). The gateway 200 can be configured to identify adverse drug events. In some embodiments, the message data for an identified adverse drug event can be held in a dedicated database and/or alert receptor (FIG. 8, 209). Upon detection of an ADE at a Publisher site $200_2$, an automated electronic alert 200A can be sent by the hub 10*h* to other Publishers 200 and/or Subscribers 300. The alert 200A can be formatted as a message integrated alert that is sent to selected participants using constraint-based rules. The rules can be set to selectively send the alert 200A to Subscribers of an associated health topic in the topic catalog. Examples of Subscribers may include the treating physician and/or hospital, a manufacturer of the drug, a clinical trial administrator, a competing manufacturer of a different alternative drug, or a governmental agency (the CDC, the FDA and the like) in generally real time using a messaging system as described above.

Figure 19:
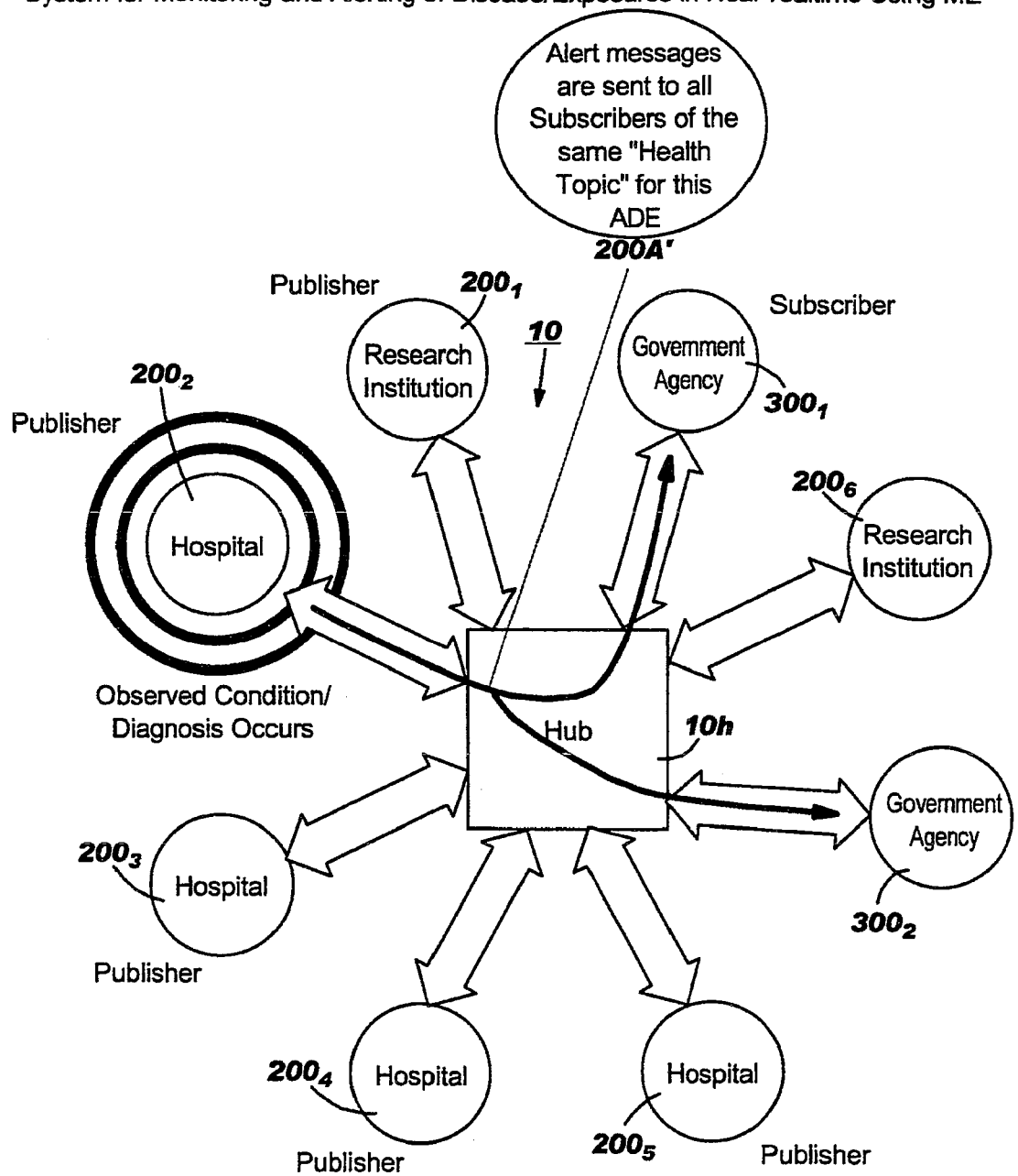
FIG. 19 is a schematic illustration of a healthcare system used to identify and generate an alert identifying of a disease outbreak, a public health risk, an environmental hazard and/or bioterrorism event according to embodiments of the present invention.

FIG. 19 illustrates that embodiments of the present invention can be used to monitor and/or identify disease outbreaks. As for the ADE alerts, disease outbreaks, certain diagnosis or exposure observations can trigger a disease/exposure alert 200A' to all or some of the participating Subscribers 300. As before, the alerts 200A' may be sent based on constraint-based rules to selected Subscribers. For example, some participating Subscribers (such as governmental agencies) may be particularly interested in prompt notifications when Publishers identify patients having diseases or exposures associated with increased mortality rates, public health risks, diseases that are considered contagious, increased numbers of patients having common diagnosis (abnormal outbreaks) and/or bioterrorism events or agents. For example, the system can monitor and identify new or unexpected increases in viral, bacterial and/or protozoan caused diseases including, but not limited to, typhoid, tuberculosis, polio, small pox, a plague (bubonic), ebola, marburg, avian flu, West Nile Virus, SARS (severe acute respiratory syndrome), hepatitis and HIV. The system can also monitor and identify for bioterrorism events or agents or environmental hazards, such as anthrax exposure, food poisonings, e coli exposures, Creutzfeldt-Jakob Disease, radiation exposure, ricin exposure, asbestos exposure, and lead exposure. A more complete list of potential bioterrorism agents can be found at the CDC website: www.bt.cdc.gov/agent/agentlist.asp The alerts 200A' can be sent in substantially real time from a Publisher source 200 via the hub 10*h* to the Subscriber 300. In particular embodiments, the periodicity of the data transmission from a Publisher to one or more approved Subscribers can vary according to a Subscriber's request and/or a Publisher's collection of relevant data. A Publisher 200 can be configured to stream patient data and correlate the data generally or substantially continuously (and may do so continuously notwithstanding any computer or power disruptions or outages) so that a suspect disease can be promptly identified upon admission, lab test and/or discharge.

The monitoring can be used to provide generally real-time disease monitoring for regulatory agencies and/or payors, such as insurance companies. Early detection and monitoring by payors may allow patients to be placed in appropriate or more aggressive treatment programs or therapies, potentially reducing healthcare costs, particularly for diseases where early detection and disease management are beneficial to reduce costs, increase longevity and/or decrease mortality rates.

Embodiments of the invention can be used to integrate patent data across disparate (inter and intra) clinical systems, provide clinical quality reviews and oversight and potentially reduce the number of errors that can arise during medical treatment. The systems can be used to monitor clinical performance, process variation and provide business related data such as cost analysis. A single Publisher can support multiple Subscribers and publish clinical data in different formats as discussed above (such as using HL7 messages, short text messages, emails and the like) and publish to different devices such as PDA's, personal computers, mainframes (directly to repository databases), portable wireless communication devices cellular phones/communications and the like.

The publishing sites (data source organizations) can control publication of its own patient data and approve or deny a Subscriber (data review organization) request for data. Publishers can comply with HIPAA privacy regulations by transmitting patient data (non-directly identifiable patient data as appropriate) using high security standards around authentication and encryption.

The systems can integrate pharmacy, laboratory and admission/discharge systems and collect relevant data streams (such as HL7 data streams) and correlate the patient data so that a relatively comprehensive record can be forwarded to an approved Subscriber. The system is configured to control and/or verify that only approved data is securely published in an agreed-upon manner (such as without patient identifier data).

The systems can use a "publish and subscribe" protocol that routes requested data based on content (clinical topics for healthcare systems) and a subscription entitlement that is linked to a privacy and/or authorization level. The architecture is relatively flexible, scalable and configured to facilitate easy adoption at participant sites.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. In the claims, means-plus-function clauses, where used, are intended to cover the structures described herein as performing the recited function and not only structural equivalents but also equivalent structures. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed is:

1. A computer program product for providing Publisher data to a collaborative healthcare data sharing system over a computer network, the computer program product comprising:

a computer readable storage medium having computer readable program code embodied in said medium, said computer-readable program code comprising:

computer program code that enables receipt and tracking of a subscription to receive electronic patient clinical data from a Publisher database;

computer program code that receives and correlates clinical data from a plurality of different data sources and places data related to a particular patient into a respective electronic clinical data record having a plurality of electronically searchable data fields;

computer program code for sharing the clinical data with a subscriber to the Publisher database, wherein the subscriber requests the clinical data via the subscription;

computer program code for specifying a set interval of time for accumulating patient-specific clinical data; and computer readable program code configured to automatically store certain patient-specific clinical data in a temporary cache for the set interval of time to correlate later arriving patient-specific related clinical data arriving during the set interval with current or previously received patient-specific data and thereby compile all related patient-specific clinical data arriving during the set interval into respective clinical data records prior to storing the related patient-specific patient-specific clinical data in the Publisher database.

2. A computer program product according to claim 1, further comprising:

computer readable program code configured to electronically store the clinical data records in a Publisher database for a limited time from which one or more of the clinical data records are published to a subscriber to the Publisher database.

3. A computer program product according to claim 1, further comprising:

computer readable program code configured to place electronic healthcare clinical data into a standard message format thereby forming clinical data messages;

computer readable program code configured to selectively remove patient identifier data from clinical data messages; and computer readable program code configured to selectively transmit clinical data messages for publication to a Subscriber.

4. A computer program product according to claim 1, further comprising computer readable program code configured to format the clinical data into electronic messages comprising open standard formats of data.

5. A computer program product according to claim 4, further comprising computer readable program code configured to collect clinical data and convert certain data into industry accepted laboratory and pharmacy codes.

6. A computer program product according to claim 1, further comprising computer readable program code configured to automatically electronically review incoming clinical data and normalize said clinical data into a standardized data message format.

7. A computer program product according to claim 1, further comprising computer readable program code that is configured to define a privacy level that controls at least one of: (a) which of a plurality of Subscribers can electronically receive clinical data from each of said data sources: and (b) what clinical data each of the plurality of Subscribers can receive from each of said data sources.

8. A computer program product according to claim 1, further comprising computer readable program code that is configured to receive a publication request from the Subscriber at a web portal via an Administrative Server for a selected healthcare topic.

9. A computer program product according to claim 8, further comprising computer readable program code configured to allow a Publisher to selectively approve the publication request upon local decisional rules.

10. A computer program product according to claim 1, further comprising computer readable program code configured to electronically monitor and automatically identify an adverse drug event from said clinical data and send the identified adverse drug event as an alert.

11. A computer program product according to claim 1, further comprising computer readable program code configured to automatically monitor and electronically identify a health event from the clinical data and alert the Subscriber.

12. A computer program product according to claim 1, further comprising computer readable program code configured to define rule criteria for the Subscriber request for data to electronically determine the relevant clinical data records.

13. A computer program product according to claim 12, further comprising computer readable program code configured to automatically electronically search electronic clinical data records using the defined rule criteria for the Subscriber request.

14. A computer program product according to claim 1, further comprising computer readable program code configured to automatically electronically transmit selected clinical data records for publication to the Subscriber.

15. A computer program product according to claim 14, further comprising computer readable program code configured to remove personal identifier data from said selected clinical data records before transmitting said selected clinical data records as an outgoing publication to the Subscriber.

16. A computer program product according to claim 1, further comprising computer readable program code configured to communicate with a global Anonymous Global Patient Identifier Server and/or Module ("AGPI") to assign a unique patient identifier to each outgoing data record publication so that the outgoing publication is traceable but devoid of personal identifying data.

17. A computer program product according to claim 1, further comprising computer readable program code configured to map data elements of electronic clinical data records into standardized HL 7 messages.

18. A computer program product according to claim 1, further comprising computer program code configured to convert non-standard HL 7 observation messages in electronic clinical data records to standard HL 7 messages.

19. A computer program product according to claim 1, further comprising computer program code configured to convert drug orders from a non standard HL 7 observation to a standard pharmacy order message in an electronic clinical data record.

20. A computer program product according to claim 1, further comprising computer program code configured to map local Publisher codes for Admission Source and Discharge Disposition to HL 7 recommended codes and/or data fields.

21. A computer program product according to claim 1, further comprising computer program code configured to map local codes for laboratory observations to systemwide codes of laboratory tests/results.

\* \* \* \* \*